(12) United States Patent
Hashimoto et al.

(10) Patent No.: US 7,436,501 B2
(45) Date of Patent: Oct. 14, 2008

(54) MICROSCOPE

(75) Inventors: Takeshi Hashimoto, Hachioji (JP);
Shinichi Hayashi, Hachioji (JP);
Junichi Kitagawa, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/363,082

(22) Filed: Feb. 28, 2006

(65) Prior Publication Data

US 2006/0238745 A1 Oct. 26, 2006

(51) Int. Cl.
*G01N 21/64* (2006.01)
*G01N 21/65* (2006.01)

(52) U.S. Cl. .................. 356/73; 356/301; 356/318; 356/417; 250/458.1

(58) Field of Classification Search .............. 356/301, 356/317, 318, 417, 73; 250/458.1
See application file for complete search history.

(56) References Cited

U.S. PATENT DOCUMENTS

| | | | | |
|---|---|---|---|---|
| 6,108,081 | A * | 8/2000 | Holtom et al. | 356/301 |
| 2003/0011765 | A1 | 1/2003 | Xie et al. | |
| 2003/0160955 | A1* | 8/2003 | Xie et al. | 356/301 |
| 2004/0051867 | A1* | 3/2004 | Brestel et al. | 356/318 |
| 2005/0168735 | A1* | 8/2005 | Boppart et al. | 356/301 |

FOREIGN PATENT DOCUMENTS

| | | |
|---|---|---|
| JP | 2000-310799 | 11/2000 |
| JP | 2000-338405 | 12/2000 |
| JP | 2002-520612 | 7/2002 |
| JP | 2006023387 | 1/2006 |
| WO | WO 00/04352 | 1/2000 |
| WO | WO 02/06778 A1 | 1/2002 |

OTHER PUBLICATIONS

Paul A. Klekotka et al., "Mammary Epithelial Cell-Cycle Progression via the a2b1 Integrin," American Journal of Pathology, vol. 159 ( No. 3), p. 983-992, (Sep. 3, 2001).

Darren Locke et al., "FcRy-independent Signaling by the Platelet Collagen Receptor Glycoprotein VI," The Journal of Biological Chemistry, vol. 278 ( No. 17), p. 15441-15448, (Apr. 25, 2003).

None, "The Principles of Nerve Cell Communication," Alcohol, Health & Research World, vol. 21 ( No. 2), p. 107-108, (Jun. 22, 1997).

Diane S. Lidke et al., "Coordination of the two heads of myosin during muscle contraction," PNAS, vol. 99 ( No. 23), p. 14801-14806, (Nov. 12, 2002).

Warren R. Zipfel et al., "Live tissue intrinsic emission microscopy using multiphoton-excited native fluorescence and second harmonic generation," PNAS, vol. 100 ( No. 12), p. 7075-7080, (Jun. 10, 2003).

* cited by examiner

*Primary Examiner*—F. L. Evans
*Assistant Examiner*—Abdullahi Nur
(74) *Attorney, Agent, or Firm*—Pillsbury Winthrop Shaw Pittman LLP

(57) ABSTRACT

In one or more embodiments, a microscope has a first pulsed laser and a second pulsed laser arranged to irradiate a specimen. Coherent Raman scattering light emanated from the irradiated specimen is extracted, along with multiphoton excitation fluorescence and a second harmonic wave. One or more detectors detect the extracted coherent Raman scattering light, the extracted fluorescence, and the second harmonic wave. A single specimen can simultaneously be observed with respect to either parallel or selective observations of the two-photon excitation fluorescence, the second harmonic wave, and the coherent Raman scattered light.

30 Claims, 15 Drawing Sheets

MICROSCOPE

CROSS-REFERENCE TO RELATED APPLICATIONS

This application is related to Japanese Application No. 2004-199554 filed in Japan on Jul. 6, 2004, the contents of which are incorporated by this reference.

BACKGROUND OF THE INVENTION

1. Field of the Invention

The present invention relates to a microscope for observing multi-photon excitation fluorescence, coherent Raman scattering light, second harmonic wave, and the like.

2. Description of the Related Art

Conventionally, for example, as a microscope aiming at observation of depths in a living, body tissue, for example, a multiphoton excitation fluorescence microscope as shown in the publication of the Japanese unexamined patent application, Toku Kai No. 338405 has been known. For example, as the microscope aiming at observation of a living body tissue, such as collagen which forms a cell membrane, a muscular fiber, and protein sequences, for example, a second higher-harmonic-wave microscope using nano-structural dependence nature of the second harmonic wave as shown in the publication of the Japanese unexamined patent application, Toku Kai No. 2000-310799 has been known.

In molecular biology, it has been much demanded that a living activity of particles in the living body, for example, DNA, amino acid, cell organelles, etc., can be observed. Although it is possible to observe the particle in the living body to some extent in case that a conventional fluorescence microscope or multiphoton excitation fluorescence microscope is used, it is necessary to dye target particles by fluorescence pigment. However, it is not desirable to dye a living body by the fluorescence pigment, since it is foreseen that the living body is affected not a little by such facts that toxicity exists in the fluorescence pigment and free movement of the particles is hindered by the fluorescence pigment, and so on.

In recent years, as a microscope for observing three-dimensional distribution of particles in the living body without dyeing, and for observing the like, a coherent Raman scattering microscope for observing coherent anti-Stokes Raman scattering light, has been proposed, for example, as shown in the following patent documents, Toku Hyou 2002-520612, WO 02/06778A1, and US 2003/0011765.

In the multiphoton excitation fluorescence microscope, this fluorescence is observed by using such phenomenon that a sample colored with fluorescent substance is irradiated by super-short pulse laser having a pulse interval of nanosecond, picosecond, or femtosecond at a wavelength $\lambda$, and when the irradiation intensity on the sample becomes large enough, multi-photon absorption where two or more (n) of the photon having the wavelength X occurs simultaneously, and the fluorescent substance which has colored the sample is excited by wavelength of $\lambda/n$, and the fluorescence having a wavelength that is a little longer than $\lambda/n$ is emitted.

In the microscope which observes the second harmonic wave, the second harmonic wave is observed by using such phenomenon that the second harmonic wave having two fold of the frequency (the wavelength becomes a half) of the laser light entered from the sample is emitted when laser light is entered into a sample.

In the coherent Raman scattering microscope, the Raman scattering light is observed by using such phenomenon that when a sample is irradiated by excited light, photon energy of illuminating radiation receives inelastic scattering by molecular vibration of the sample, and scattered light having a wavelength which is shifted by an amount of energy equivalent to the proper frequency of a molecule of substance is produced.

By the way, recent years, in the microscope observation of organisms, there is a tendency that various observations combined by the observation techniques mentioned above is required responding to an area of interest of observation object, For example, in American Journal of Pathology, (Vol. 159, p. 983), there is a description aiming at observation of discharge of integrin molecules and specialization of collagen, at the time of cell morphogenesis of epidermic cells. For such observation, it is desired that observation is carried out in parallel, or selectively in such ways that for epidermic cells as a specimen, as for the whole cell, observation is carried out by using the multiphoton excitation fluorescence, as for collagen, it is carried out by using the second harmonic wave, and as for integrin molecules it is carried out by using the coherent Raman scattering light.

Further, for example, in Journal of Biological Chemistry, (Vol. 17, p. 15441), there is a description aiming at observation of discharge of lipid molecules from a fat cell at the time of insulin medication in the fat cell. For such observation, it is desired that observation is carried out in parallel, or selectively in such ways that for fat cells as a specimen, receptors are observed by using multiphoton excitation fluorescence, cell membranes are observed by using the second harmonic wave, and lipid molecules are by observed using the coherent Raman scattering light.

Further, for example, in Alcohol Health & Research World, (Vol. 21, p. 107), there is a description aiming at an observation of the potential difference on cell membranes in nerve cells and an observation of amino acid molecules discharge accompanying it. For such observation, it is desired that observation is carried out in parallel, or selectively in such ways that for nerve cells as a specimen, potential sensitive is observed by using the multiphoton excitation fluorescence, cell membranes are observed by using the second harmonic wave, and amino acid molecules as a target is observed by using the coherent Raman scattering light.

Further, for example, in PNAS, (Vol. 99, p. 14801), there is a description aiming at an observation of discharge of a calcium wave and sliding movement of myosin molecules having acting fiber form. For such observation, it is desired that the observation is carried out in parallel, or selectively in such way that for muscle cells as a specimen, calcium sensitive pigment is observed by using the multiphoton excitation fluorescence, actin fibers are observed by using a second harmonic wave myosin molecules are observed by using the coherent Raman scattering light.

Further, for example, in PNAS, (Vol. 100, p. 7075), there is a description aiming at diagnosis of cancer using the quantity of NADH and the degree of collapse of collagen fibers.(the degree of collapse of the collagen fibers are detectable with an intensity ratio of the second harmonic wave and the coherent Raman scattering light.) For such diagnosis, it is desired that observation is carried out in parallel, or selectively in such ways that for a cancer cell as a specimen, NADH is observed by using the multiphoton excitation fluorescence, collagen fibers are observed by using the second harmonic wave, and collagen fibers are observed by using the coherent Raman scattering light.

SUMMARY OF THE INVENTION

The microscope according to the present invention comprises a first pulsed laser generating means that generates a first pulse light having a first wavelength component, a second pulsed laser generating means that generates a second pulse light having a second wavelength component, an irradiation means which is constituted so that irradiation to a specimen can be carried out by composing the first pulse light and the second pulse light, a coherent Raman scattering light extraction means which extracts only coherent Raman scattering light from light from the specimen to which light is irradiated through the irradiation means, a multiphoton excitation fluorescence extraction means which extracts only multiphoton excitation fluorescence generated by irradiating the second pulse light to the specimen from the light emanated from the specimen to which light is irradiated through the irradiation means, a second harmonic wave extraction means that extracts only second harmonic wave generated by irradiating the second pulse light to the specimen from the light from the specimen to which light is irradiated through the irradiation means, a coherent Raman scattering photon detection means which detects the coherent Raman scattering light extracted through the coherent Raman scattering light extraction means, a multiphoton excitation fluorescence detection means which detects the multiphoton excitation fluorescence extracted through the multiphoton excitation fluorescence extraction means, and a second harmonic wave detection means that detects the second harmonic wave extracted through the second harmonic wave extraction means. The microscope according to the present invention comprises a first pulsed laser generating means that generates a first pulse light having a first wavelength, a second pulsed laser generating means that generates a second pulse light having a second wavelength, an irradiation means which is constituted so that irradiation to a specimen can be carried out by composing the first pulse light and the second pulse light, a coherent Raman scattering light extraction means which extracts only coherent Raman scattering light from light emanated from the specimen to which light is irradiated through the irradiation means, an epi-illuminated multiphoton excitation fluorescence extraction means which extracts only multiphoton excitation fluorescence generated by irradiating the second pulse light to the specimen from the light emanated from the specimen to which light irradiated through the irradiation means goes toward a direction where the light is reflected, a forward second harmonic wave extraction means that extracts only the second harmonic wave generated by irradiating the second pulse light to the specimen, from the light emanated from the specimen, where the light irradiated through the irradiation means goes toward a direction where the light transmits, an coherent Raman scattering photon detection means which detects the coherent Raman scattering light extracted through the coherent Raman scattering light extraction means, an epi-illuminated multiphoton excitation fluorescence detection means which detects the multiphoton excitation fluorescence extracted through the epi-illuminated multiphoton excitation fluorescence extraction means, and a forward second harmonic wave detection means that detects the second harmonic wave extracted through the forward second harmonic wave extraction means.

The microscope according to the present invention comprises a first pulsed laser generating means that generates a first pulse light having a first wavelength, a second pulsed laser generating means that generates a second pulse light having a second wavelength, an irradiation means which is constituted so that irradiation to a specimen can be carried out by composing the first pulse light and the second pulse light, a coherent Raman scattering light extraction means which extracts only coherent Raman scattering light from light from the specimen to which light is irradiated through the irradiation means, an epi-illuminated second harmonic wave extraction means that extracts only the second harmonic wave generated by irradiating the second pulse light to the specimen, from the light emanated from the specimen to which the light irradiated through the irradiation means goes toward a direction where the light is reflected, a forward multiphoton excitation fluorescence extraction means which extracts only the multiphoton excitation fluorescence generated by irradiating the second pulse light to the specimen from the light emanated from the specimen to which the light irradiated through the irradiation means goes toward a direction where the light transmits, a coherent Raman scattering photon detection means which detects the coherent Raman scattering light extracted through the coherent Raman scattering light extraction means, a forward multiphoton excitation fluorescence detection means which detects the multiphoton excitation fluorescence extracted through the forward multiphoton excitation fluorescence extraction means, and an epi-illuminated second harmonic wave detection means that detects the second harmonic wave extracted through the epi-illuminated second harmonic wave extraction means.

The microscope according to the present invention comprises a first pulsed laser generating means that generates a first pulse light having a first wavelength, a second pulsed laser generating means that generates a second pulse light having a second wavelength, an irradiation means which is constituted so that irradiation to a specimen can be carried out by composing the first pulse light and the second pulse light, a coherent Raman scattering light extraction means which extracts only coherent Raman scattering light from light from the specimen to which light is irradiated through the irradiation means, an epi-illuminated second harmonic wave multiphoton excitation fluorescence switching extraction means which extracts, by switching, only the second harmonic wave generated by irradiating the second pulse light to the specimen or, extracts only the multiphoton excitation fluorescence generated by irradiating the second pulse light to the specimen, from the light emanated from the specimen to which the light irradiated through the irradiation means goes toward a direction where the light is reflected, a forward second harmonic wave multiphoton excitation fluorescence switching extraction means which extracts, by switching, only the second harmonic wave generated by irradiating the second pulse light to the specimen, or, extracts only the multiphoton excitation fluorescence generated by irradiating the second pulse light to the specimen, from the light emanated from the specimen to which the light irradiated through the irradiation means goes toward a direction where the light transmits, a coherent Raman scattering photon detection means which detects the coherent Raman scattering light extracted through the coherent Raman scattering light extraction means, the epi-illuminated switching extraction light detection means which detects the light extracted through the epi-illuminated second harmonic wave multiphoton excitation fluorescence switching extraction means, and a forward switching extraction light detection means which detects the light extracted through the forward second harmonic wave multiphoton excitation fluorescence switching extraction means.

The microscope according to the present invention comprises a first pulsed laser generating means that generates a first pulse light having the first wavelength, a second pulsed laser generating means that generates a second pulse light having a second wavelength, an irradiation means which is constituted so that irradiation to a specimen can be carried out by composing the first pulse light and the second pulse light, a coherent Raman scattering light extraction means which extracts only coherent Raman scattering light from light from the specimen to which light is irradiated through the irradiation means, an epi-illuminated multiphoton excitation fluorescence extraction means which extracts only multiphoton excitation fluorescence generated by irradiating the second pulse light to the specimen from the light emanated from the specimen to which light irradiated through the irradiation means goes toward a direction where the light is reflected, an epi-illuminated second harmonic wave extraction means that extracts only the second harmonic wave generated by irradiating the second pulse light to the specimen, from the light emanated from the specimen to which the light irradiated through the irradiation means goes toward a direction where the light is reflected, a coherent Raman scattering photon detection means which detects the coherent Raman scattering light extracted through the coherent Raman scattering light extraction means, an epi-illuminated multiphoton excitation fluorescence detection means which detects the multiphoton excitation fluorescence extracted through the epi-illuminated multiphoton excitation fluorescence extraction means, an epi-illuminated second harmonic wave detection means that detects the second harmonic wave extracted through the epi-illuminated second harmonic wave extraction means, a forward multiphoton excitation fluorescence extraction means which extracts only the multiphoton excitation fluorescence generated by irradiating the second pulse light to the specimen from the light emanated from the specimen to which the light irradiated through the irradiation means goes toward a direction where the light transmits, a forward second harmonic wave extraction means that extracts only the second harmonic wave generated by irradiating the second pulse light to the specimen, from the light emanated from the specimen, where the light irradiated through the irradiation means goes toward a direction where the light transmits, a forward multiphoton excitation fluorescence detection means which detects the multiphoton excitation fluorescence extracted through the forward multiphoton excitation fluorescence extraction means, and a forward second harmonic wave detection means that detects the second harmonic wave extracted through the forward second harmonic wave extraction means.

In the microscope according to the present invention, it is desired that a predetermined wavelength band having a wavelength shorter than the wavelength of the first pulse light which is near the wavelength of the first pulse light is scanned by a wavelength of the second pulse light, and the coherent Raman scattering light is the coherent anti-Stokes Raman scattering light.

In the microscope according to the present invention, it is possible to constitute so that it has a multiphoton excitation fluorescence CARS light separation means in which a predetermined wavelength band having a wavelength longer than the wavelength of the first pulse light which is near the wavelength of the first pulse light is scanned by a wavelength of the second pulse light, and the coherent Raman scattering light is the coherent anti-Stokes Raman scattering light, and the multiphoton excitation fluorescence and the coherent anti-Stokes Raman scattering light where wavelengths may overlap at least in a part of wavelength bands are separated.

In the microscope according to the present invention, it is desired that the multiphoton excitation fluorescence CARS light separation means is constituted of the coherent anti-Stokes Raman scattering photon extraction means having a time decomposition separation means which separates the multiphoton excitation fluorescence and the coherent anti-Stokes Raman scattering light by time decomposition.

In the microscope according to the present invention, it is desired that the time-resolved separation means comprises a Kerr gate which changes a polarization direction of the linear polarized light of the light transmitted when the light enters at an angle, a gate light incidence means which makes the second pulse light enter at an angle to the Kerr gate, at the same timing as the timing in which the coherent anti-Stokes Raman scattering light enters into the Kerr gate, a first polarization component that changes the multiphoton excitation fluorescence into linear polarized light, and a second polarization component that transmits linear polarized light, where a direction of polarization was changed by transmitting the Kerr gate, and intercepts linear polarized light which does not change in polarization direction when it transmits the Kerr gate.

In the microscope according to the present invention, it is desired that the multiphoton excitation fluorescence CARS light separation means is constituted of the modulation means which generates modulated coherent anti-Stokes Raman scattering light, and a detection device which serves as both of the coherent anti-Stokes Raman scattering photon detection means and the multiphoton excitation fluorescence detection means, and receives both the modulated coherent anti-Stokes Raman scattering light and the multiphoton excitation fluorescence, and detects a modulation component and a non-modulation component by separating them from the received light.

In the microscope according to the present invention, it is desired that the modulation means is constituted of a modulator which modulates the first pulse light and, the detection device is constituted of a lock-in detector. In the microscope according to the present invention, it is desired that a predetermined wavelength band is scanned by the first pulse light and, the second pulse light is fixed to an optimal wavelength for multiphoton excitation. In the microscope according to the present invention, it is desired that it comprises a laser light selection means having a switching means which switches ON/OFF of the first pulsed laser generating means and the second pulsed laser generating means, and a control means to control the laser light selection means.

In the microscope according to the present invention, it is desired that it comprises an image processing apparatus which processes a signal detected through the coherent Raman scattering photon detection means, the multiphoton excitation fluorescence detection means, and the second harmonic wave detection means, an image display apparatus which displays an image processed by the image processing apparatus, and a scanning means which scans the light irradiating the specimen in the direction of two dimensions, wherein the control means controls the laser light selection means and the scanning means so that an observation image by the coherent Raman scattering light, an observation image by the multiphoton excitation fluorescence, and an observation image by the second harmonic wave are displayed simultaneously or selectively, through the image processing apparatus and the image display apparatus, at a position corresponding to an area of interest of e the specimen in the display screen of the image display apparatus, control the laser light selection means and the scanning means.

In the microscope according to the present invention, it is desired that the first pulsed laser generating means is a pulsed laser light source which oscillates the pulsed laser beam having wavelength width of picosecond, and the second pulsed laser generating means is a pulsed laser light source which oscillates the pulsed laser beam having pulse width of femtosecond.

In the microscope according to the present invention, it is desired that the coherent Raman scattering light extraction means is constituted so that it enables to switch an extraction of only the coherent Raman scattering light from the light which is emanated from the specimen and goes toward a direction in which the light irradiated through the irradiation means is reflected, an extraction of only the coherent Raman scattering light from the light which is emanated from the specimen and goes toward the direction in which the light irradiated through the irradiation means transmits, and an extraction of only both of the coherent Raman scattering light from the light which is emanated from the specimen and goes toward a direction in which the light irradiated through the irradiation means transmits, and the coherent Raman scattering light from the light which is emanated from the specimen and goes toward a direction in which the light irradiated through the irradiation means is reflected.

These and other features and advantages of the present invention will become apparent from the following detailed description of the preferred embodiments when taken in conjunction with the accompanying drawings.

DETAILED DESCRIPTION OF THE PREFERRED EMBODIMENTS

Prior to explaining embodiments, reasons why the constitution of the present invention has been made as well as functions and advantages according to the present invention will be explained.

According to the microscope of the present invention, the second harmonic wave, the multiphoton excitation fluorescence, and the coherent Raman scattering light can be separated, extracted and detected.

Before explaining the features concretely, principle of generation of the coherent anti-Stokes Raman scattering light and the coherent Stokes Raman scattering light will be explained.

Figure 1:
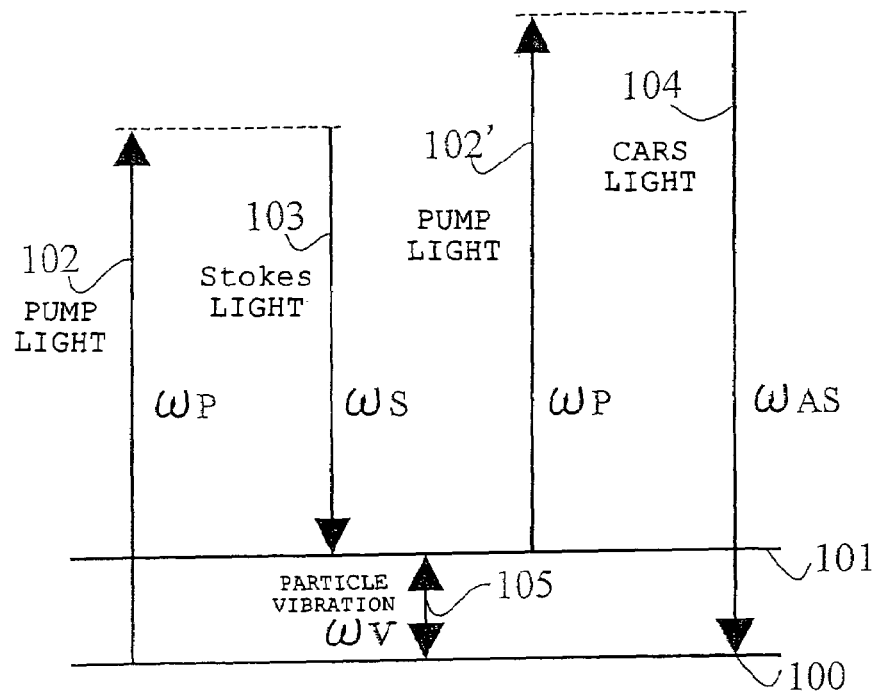
FIG. 1 is a diagram showing relations among pump light in CARS, Stoke light, anti-Stoke light, and a frequency of a particle.

First, the principle of generation of the coherent anti-Stokes Raman scattering light is explained as follows. As shown in FIG. 1, when difference of frequency $\omega_P$ of pump light 102 and frequency $\omega_S$ of Stokes light 103 are coincided with natural-frequency $\omega_V$ of a particle 105 at the light condensing position in a specimen, the particle 105 at a ground state 100 generates resonance vibration with the frequency $\omega_V$, and an excitation state 101 occurs. Then, a part of pump light 102' having frequency $\omega_P$ receives the Doppler modulation of the natural-frequency $\omega_V$ of the particle 105, and the coherent anti-Stokes Raman scattering light (CARS light) 104 having frequency $\omega_{AS}$ is generated. At this time, there is the following relation;

$$\omega_{AS} = \omega_P + \omega_V = 2\omega_P - \omega_S$$

Therefore, if frequency $\omega S$ of the Stokes light 103 is scanned while fixing the frequency $\omega P$ of the pump light 102, the natural frequency spectrum of the particle 105 can be observed. Since the natural frequency spectrum changes by a kind of particles, even when two or more kinds of particles exist simultaneously, the kind of each particle can be specified.

Generated intensity $I_{AS}$ of the coherent Raman scattering light as shown in the following equation, is proportional to the product of a square of intensity $I_P$ of the pump light and intensity $I_S$ of the Stokes light.

$$I_{AS} \propto I_P^2 I_S$$

In such way, the coherent anti-Stokes Raman scattering light 104 is strongly generated only in the condensing position of the pump light and the Stokes light in the specimen. Generated intensity IAS of the coherent Raman scattering light is proportional also to a square of the amount of the particle 105 existing locally. Therefore, by scanning spatially the condensing position of the pump light and the Stokes light within the specimen, it is possible to obtain a space distribution in the specimen of a specific particle.

Next, generation principle of the coherent Stokes Raman scattering light will be explained using FIG. 2.

When laser pulse whose wavelength is shorter than that of the pump light is used instead of the laser pulse of the Stokes light mentioned above, the wavelength of the coherent Raman scattering light becomes longer than that of the pump light. This is called coherent Stokes Raman scattering light (CSRS light). And, laser pulse whose wavelength is shorter than that of the pump light at this time is called anti-Stokes light.

Figure 2:
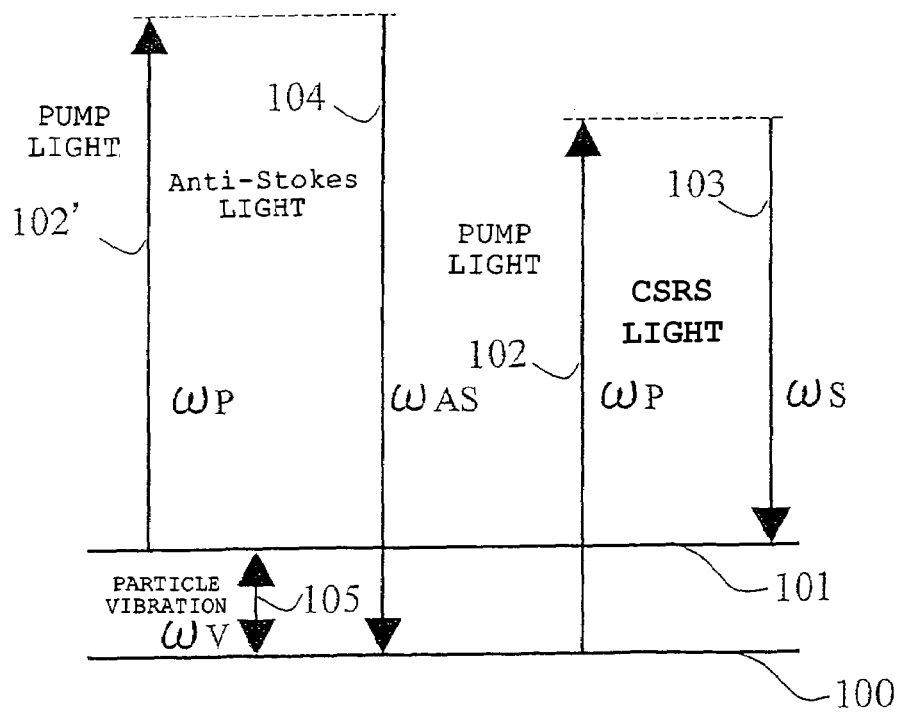
FIG. 2 is a diagram showing relations among the pump light in CSRS, anti-Stoke light, Stoke light, and a frequency of a particle.

As shown in FIG. 2, when difference between frequency $\omega P$ of the pump light 102' and frequency $\omega AS$ of the anti-Stokes light 104 is coincided with natural-frequency $\omega V$ of the particle 105 at the condensing position in a specimen, the particle 105 at the ground state 100 generates a resonance vibration with the frequency $\omega V$, and it becomes to the excitation state 101. Then, a part of pump light 102 having frequency $\omega P$ receives the Doppler modulation of natural-frequency $\omega V$ of the particle 105, and CSRS light 103 having frequency $\omega_{AS}$ is generated. At this time, there is the following relation.

$$\omega_S = \omega_P - \omega_V = 2\omega_P - \omega_{AS}$$

Therefore, if frequency $\omega AS$ of the anti-Stokes light 104 is scanned while fixing the frequency $\omega P$ of the pump light 102, the natural frequency spectrum of a particle 105 can be observed. Since the natural frequency spectrum changes by the kind of particle, even when two or more kinds of particles exist simultaneously, the kind of each particle can be specified.

In such way, the CSRS light has the same character as the CARS light except a fact that the CARS light has a longer wavelength than that of the pump light. Further, since the wavelength of the CSRS light is longer than that of the anti-Stokes light, it has a feature such that there is almost no overlapping with wavelength of the multiphoton excitation fluorescence generated by excitation of the anti-Stokes-light pulse.

In generation process of the coherent Raman scattering light, self-fluorescence having a wavelength longer than that of the pump light is generated from the object of irradiation by the pump light. For this reason, if observation using the coherent Stokes Raman scattering light having a wavelength longer than that of the pump light by the usual visible light domain is carried out, overlapping with the self-fluorescence is generated, and accordingly, trouble arises easily in the observation.

By the way, the second harmonic wave has a wavelength of a half of that of the excitation light which is the Stokes light or the anti-Stokes light. Multiphoton excitation fluorescence has a wavelength shorter than that of the excitation light. In the microscope according to the present invention, considering that each wavelength band of the second harmonic wave, the multiphoton excitation fluorescence and the pump light for observing the coherent Raman scattering light does not overlap mutually. And considering that a visible light domain is effectively used as a wavelength domain of the observation light, the second harmonic wave is used at the shortest wavelength domain, and the multiphoton excitation fluorescence is used at a wavelength band longer than it. And, considering that these wavelengths, the excitation light and the pump light are made not to overlap each other, the wavelength domain of the pump light becomes a near-infrared domain.

Thus, in the microscope according to the present invention, the wavelength domain of the pump light becomes settled inevitably in a near-infrared domain. In the microscope according to the present invention, if it is constituted such that wavelength of the second pulse light of is near the wavelength of the first pulse light, and a predetermined wavelength band of wavelength shorter than the wavelength of the first pulse light is scanned, and the coherent Raman scattering light is the coherent Stokes Raman scattering light, since each wavelength of the second harmonic wave, the multiphoton excitation fluorescence, and the coherent Stokes Raman scattering light does not overlap, each wavelength can be detected in separated states, respectively.

In this case, since the self fluorescence generated in a near-infrared domain has weak intensity compared with the coherent Stokes Raman scattering light, no trouble in the observation occurs. On the other hand, as the wavelength of the anti-Stokes Raman scattering light is shorter than that of the pump light, no influence of the self fluorescence by the pump light is suffered. However, the intensity of the anti-Stokes light is generally weak about 3~4 orders comparing with the intensity of the pump light or the Stokes light.

And, the multiphoton excitation fluorescence has a wavelength shorter than that of the excitation light as mentioned above. Therefore, when the second harmonic wave, the multiphoton excitation fluorescence, and the coherent Stokes Raman scattering light are observed, there is a case that the anti-Stokes Raman scattering light and the multiphoton excitation fluorescence, the wavelength may overlap in some part of wavelength bands, and accordingly, a case where detection of the anti-Stokes Raman scattering light having a weak intensity becomes difficult may occur.

In the microscope according to the present invention, if it comprises a multiphoton excitation fluorescence CARS light separation means which separates the multiphoton excitation fluorescence and the coherent anti-Stokes Raman scattering light, wherein the wavelength of the second pulse light is near the wavelength of the first pulse light, and it scans a predetermined wavelength band having a wavelength longer than the wavelength of the first pulse light, and the coherent Raman scattering light is coherent anti-Stokes Raman scattering light, and any of wavelengths may overlap at least in some part of wavelength band, each of wavelengths can be detected in a separated state, respectively.

Therefore, according to the microscope of the present invention responding to an object observed to one specimen as at least by using one microscope, all of the multiphoton excitation fluorescence observation, the second harmonic wave observation, and the coherent Raman scattering light observations can be carried out in parallel.

The multiphoton excitation fluorescence CARS light separation means can be constituted of the coherent anti-Stokes Raman scattering light extraction means having a time-resolved separation means which separates the multiphoton excitation fluorescence and the coherent anti-Stokes Raman scattering light by time-resolved method.

Or, the multiphoton excitation fluorescence CARS light separation means can be constituted of a modulation means which generates modulated coherent anti-Stokes Raman scattering light, and a detection means which serves as both of the coherent Raman scattering light detection means and the multiphoton excitation fluorescence detection means, wherein the detection means receives both of the modulated coherent anti-Stokes Raman scattering lights and the multiphoton excitation fluorescences, and separates a modulated component and non-modulation component from the received light and detects them.

According to the microscopes of the present invention, as mentioned above, it is constituted so that a predetermined wavelength band near the wavelength of the first pulse light may be scanned by the second pulse light.

There is an absorption spectrum in the multiphoton excitation fluorescence, and a luminescence intensity of the multiphoton excitation fluorescence changes by scanning the wavelength of the Stokes light. Then, if it is constituted, like the microscope of the present invention, that it may be scanned by the second pulse light, the wavelength of the second pulse light used as the Stokes light can be adjusted so that the luminescence intensity of the multiphoton excitation fluorescence may become to the maximum, and the multiphoton excitation fluorescence can be detected efficiently.

Each of absorption spectra of multiphoton-excitation-fluorescence pigment differs, respectively. Therefore, if it is scanned by the wavelength of the second pulse light, a fluorescence pigment can be identified from change of the luminescence intensity of the multiphoton excitation fluorescence.

In the second harmonic wave, owing to nonlinear effect, influences by the Stokes light having a high peak output value with narrower pulse width compared with that of the pump light becomes dominating. And, the generation efficiency of the second harmonic wave is dependent on the wavelength of excitation light (in this case, the Stokes light). Then, if it is scanned by a wavelength of the second pulse light, it is possible to adjust so that the generation efficiency of the second harmonic wave may become the optimal.

In the microscope of the present invention, the wavelength of the second pulse light may be fixed as the optimal wavelength for multiphoton excitation, while a predetermined wavelength band is scanned by the first pulse light, In the microscope of the present invention, the second pulse light (the Stokes light or the anti-Stokes light) performs a function as excitation light in the multiphoton excitation fluorescence observation and the second harmonic wave observation. When a scanning is carried out by the wavelength of the second pulse light used as Stokes light or anti-Stokes light, since an absorption spectrum changes, the luminous efficiency of fluorescence changes.

On the other hand, even if the scanning is carried out by the pump light, the luminous efficiencies of the multiphoton excitation fluorescence and the second harmonic wave do not change. Accordingly, by using a wavelength by which the luminous efficiency of the multiphoton excitation fluorescence, or the second harmonic wave becomes the optimal is used as Stokes light or anti-Stokes light, the coherent Raman scattering light can be detected, while detecting the multiphoton excitation fluorescence or the second harmonic wave in the optimal luminous condition.

By using laser light having pulse width of femtosecond as excitation light, luminous efficiencies of the multiphoton excitation fluorescence and the second harmonic wave become good, comparing with a case that the laser light having pulse width of picosecond is used.

Therefore, in the microscope of the present invention, it is desired that the first pulsed laser generating means is constituted of a pulsed laser light source which oscillates the pulsed laser beam having the wavelength width of picosecond, and the second pulsed laser generating means is constituted of a pulsed laser light source which oscillates the pulsed laser beam having the wave width of femtosecond.

In the microscope according to the present invention, in each of the light which is emanated from the said specimen and goes toward the direction where the light irradiated through the irradiation means is reflected, or in the light which is emanated from the specimen and goes toward the direction where the light irradiated through the irradiation means transmits, respectively, if a switching means which switches and extracts the second harmonic wave and the multiphoton excitation fluorescence is arranged, it is possible to select an observation technique in which the light intensity more suitable for the observation is obtained from vertical-illumination observation or penetration observation when the second harmonic wave and the multiphoton excitation fluorescence are observed, In the microscope according to the present invention, the coherent Raman scattering light extraction means is constituted so that by switching, it enables to select extraction of only the coherent Raman scattering light from the light which is emanated from the specimen and goes toward a direction in which the light irradiated through the irradiation means is reflected, extraction of only the coherent Raman scattering light from the light which is emanated from the specimen and goes toward the direction in which the light irradiated through the irradiation means transmits, and extraction of only both of the coherent Raman scattering light from the light which is emanated from the -specimen and goes toward a direction in which the light irradiated through the irradiation means transmits and the coherent Raman scattering light from the light which is emanated from the specimen and goes toward a direction in which the light irradiated through the irradiation means is reflected. By such constitution mentioned above, it is possible to select an observation technique in which the light intensity suitable for observation is obtained.

In the microscope according to the present invention, if a laser light selection means having the first pulsed laser generating means and a switching means which switches ON/OFF of the second pulsed laser generating means, and a control means which controls the laser light selection means are arranged, a desired observation technique can be chosen by selecting laser light according to the area of interest of an object of observation. Moreover, the laser irradiation to the area of interest of the object of observation can be suppressed to necessary minimum. Accordingly, the damage to the specimen and fading of fluorescence can also be suppressed considerably.

In the microscope-according to the present invention, observation can be carried out with a desired observation technique corresponding to the object for every area of interest of object of the observation on single display screen, by constituting such that it comprises an image processing apparatus which processes a signal detected through the coherent Raman scattering light extraction means, the multiphoton excitation fluorescence and the second harmonic wave detection means, an image display apparatus which displays an image processed by the image processing apparatus, and a scanning means which scans the light irradiating the specimen in the direction of two dimensions, wherein a control means is constituted so that it may control the laser light selection means and the scanning means so as to display an observation image by the coherent Raman scattering light, an observation image by the multiphoton excitation fluorescence, and an observation image by the second harmonic wave, simultaneously or selectively, at a position corresponding to an area of interest of the specimen in the display screen of the image display apparatus through the image processing apparatus and the image display apparatus.

First Embodiment

Hereafter, embodiments of the present invention will be explained using drawings. In diagrammatic charts of the drawings in the following embodiments, the following expressions are used: SHG denotes second harmonic wave, 2-P denotes multiphoton excitation fluorescence, Anti-Stokes denotes anti-Stokes light, Pump denotes pump light, CSRS denotes coherent Raman scattering light, Stokes denotes Stokes light, CARS denotes the coherent Raman scattering light, and 1-P denotes single photon excitation fluorescence. These symbols are commonly used in each of the following embodiments.

Figure 3:
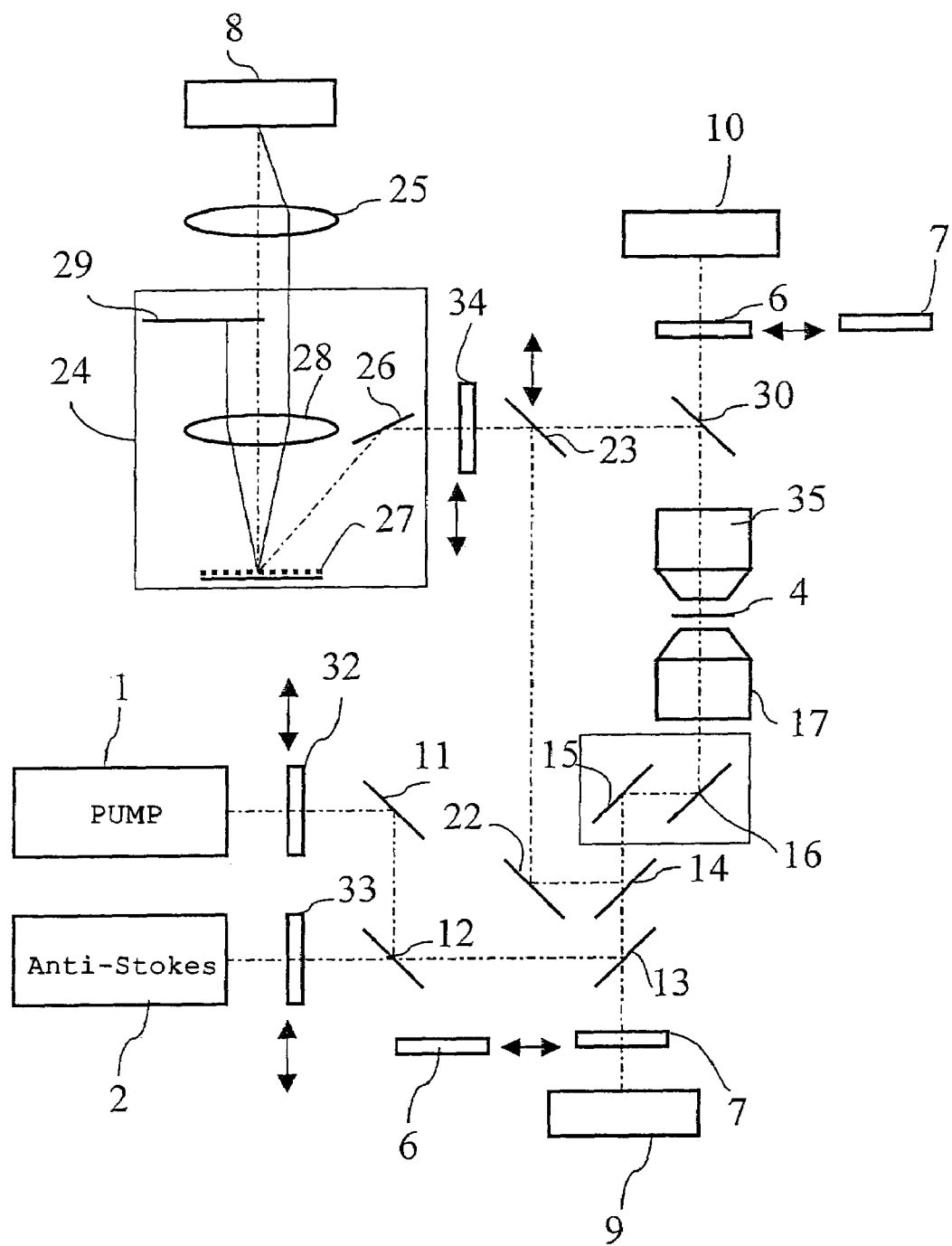
FIG. 3 is an outlined diagram showing an optical composition of the microscope system of the first embodiment according to the present invention.
Figure 4:
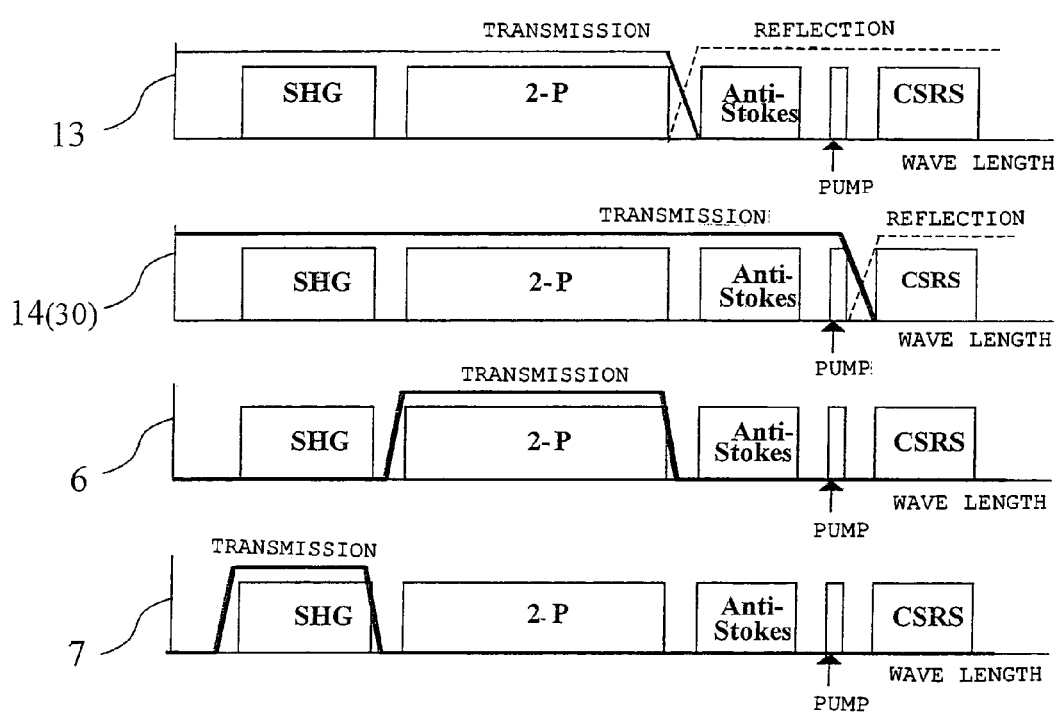
FIG. 4 is a diagrammatic chart showing optical characteristics of a dichroic mirror and a band pass filter used for the microscope in the first embodiment.

FIG. 3 is a diagram showing an optical composition of the microscope of the first embodiment according to the present invention. FIG. 4 is a diagrammatic chart showing optical characteristics of a dichroic mirror and a band pass filter used for the microscope in the first embodiment.

A microscope of the first embodiment comprises a first pulsed laser generating means 1 that generates a first pulse light having a first wavelength component, a second pulsed laser generating means 2 which generates a second pulse light having a second wavelength component, an irradiation means (symbol is omitted) which is constituted so that irradiation to a specimen 4 can be carried out by composing the first pulse light and the second pulse light, a coherent Raman scattering light extraction means (symbol is omitted)which extracts only coherent Stokes Raman scattering light from light from the specimen 4 to which irradiating light is irradiated through the irradiation means, a two-photon excitation fluorescence extraction means 6 which extracts only two-photon excitation fluorescence generated by irradiating the second pulse light to the specimen 4 from the light emanated from the specimen 4 to which irradiating light is irradiated through the irradiation means, a second harmonic wave extraction means 7 which extracts only light having the second harmonic wave component generated by irradiating the second pulse light to the specimen 4 from the light emanated from the specimen 4 to which irradiating light is irradiated through the irradiation means, a coherent Stokes Raman scattering light detection means 8 which detects the coherent Stokes Raman scattering light, a vertically illuminated photon detection means 9 and a forward light detection means 10 which detect two-photon excitation fluorescence or the second harmonic wave.

The first pulsed laser generating means 1 is constituted of a pulsed laser light source which generates pulse light having pulse width of picosecond at wavelength, for example, about 900 nm as the first pulse light.

The second pulsed laser generating means 2 is constituted of a predetermined wavelength band in which the wavelength is near the wavelength of the first pulse light, and shorter than the wavelength of the first pulse light, a pulsed laser light source which generates pulse light having pulse width of femtosecond at a predetermined wavelength band in which the wavelength is near the wavelength of the first pulse light, and shorter than the wavelength of the first pulse light, for example, about 700-900 nm as the second pulse light. Further, the second pulsed laser generating means 2 is constituted so that scanning may be carried out by using the wavelength of the second pulse light within the predetermined wavelength band (about 700-900 nm).

And, in the microscope of embodiment 1, it is constituted so that the first pulse light functions as pump light, and the second pulse light functions as anti-Stokes light.

An irradiation means is constituted of a mirror 11, a half mirror 12, dichroic mirrors 13 and 14, galvanometer mirrors 15 and 16, and an objective lens 17.

The half mirror 12 is arranged on an optical path where the first pulse light and second pulse light are crossed.

The dichroic mirror 13 has optical characteristics so that light having wavelength below the wavelength band (for example, about 500-650 nm) of two-photon excitation fluorescence may transmit it, and it may reflect the light having wavelength longer than the wavelength band (for example, about 700-900 nm) of the anti-Stokes light.

The dichroic mirror 14 has optical characteristics so that light having wavelength below the wavelength band (for example, about 900 nm) of pump light may transmit it, and it may reflect the light having wavelength longer than the wavelength band of the pump light.

The galvanometer mirrors 15 and 16 are constituted so that a light-condensing position of illuminating radiation in a specimen 4 may be scanned in the direction of two dimensions.

The coherent Raman scattering light extraction means is constituted of E-CSRS (EPI-DETECTED COHERENT STOKES RAMAN) light extraction means (symbol is omitted) which extracts the coherent Stokes Raman scattering light from the light emanated from the specimen 4 which goes toward the direction in which the light irradiated through the irradiation means is reflected, and F-CSRS (FORWARD-DETECTED COHERENT STOKES RAMAN) light extraction means (symbol is omitted) which extracts the coherent Stokes Raman scattering light from the light emanated from the specimen 4 which goes toward the direction which the light irradiated through the irradiation means transmits.

The E-CSRS-light extraction means is constituted of the dichroic mirror 14, a mirror 22, a half mirror 23, a spectroscope 24, and a lens 25.

The spectroscope 24 is constituted of a mirror 26 which leads incidence light to a spectrum element 27 which consists of a grating etc., a distributed projection lens 28 which projects the light distributed by the spectrum element 27, and a shading component 29 arranged so that the coherent Stokes Raman scattering light may pass and the other light may be intercepted.

The F-CSRS-light extraction means is constituted of a dichroic mirror 30 having the same optical characteristics as the dichroic mirror 14, the half mirror 23, the spectroscope 24 and the lens 25.

The half mirror 23 is arranged on the optical path where the light reflected by the mirror 22 and the light reflected by the dichroic mirror 30 are crossed.

The half mirror 23 and another mirror (illustration is omitted) are arranged on a slider (illustration is omitted), and it is constituted so that it may switch to select one of three conditions, namely, a condition where the half mirror 23 is arranged on the slider (illustration is omitted), a condition where the half mirror 23 has been removed from the optical path via the slider, or a condition where another mirror (illustration is omitted) is used from the half mirror 23 by switching.

In FIG. 3, the half mirror 23 is arranged on the optical path, where a condition in which the CSRS light of both the E-CSRS light and the F-CSRS light can be extracted is shown. When the half mirror 23 is removed from the optical path, only the F-CSRS light is extracted, and when switching to another mirror (illustration is omitted), only the E-CSRS light is extracted.

In the coherent stokes Raman scattering light extraction means, as P-CSRS (POLARIZATION COHERENT STOKES RAMAN) light extraction means (symbol is omitted) which extracts polarized type coherent Stokes Raman scattering light, a polarizer 32 which converts into a predetermined linear polarized light is arranged between the first pulsed laser generating means 1 and the mirror 11, and a polarizer 33 which converts into a linear polarized light having a different angle from that of the linear polarized light which is converted with the polarizer 32 is arranged between the second pulsed laser generating means 2 and the half mirror 12, and a light analyzer 34 in which the linear polarized light of the coherent Stokes Raman scattering light transmits and non-resonance scattering light is intercepted is arranged between the half mirror 23 and the spectroscope 24. The light analyzer 34 is arranged so that it can be attached and detached via the slider etc., respectively.

By inserting the P-CSRS light extraction means on the optical path, by irradiating to a specimen the first pulse light and the second pulse light which have been converted into the linear polarized light having different oscillating directions, respectively, and further by extracting only the linear polarized light component of a specific direction from the scattering light the non-resonant Raman scattering component as background noise is removed, and accordingly, the coherent Stokes Raman scattering light can be detected with high sensitivity,.

The two-photon excitation fluorescence extraction means 6 is constituted of a band pass filter where only the light having a wavelength of the wavelength band (for example, about 500-650 nm) of the two-photon excitation fluorescence transmits, and the light having a wavelength other than the wavelength mentioned above is intercepted.

The second harmonic wave extraction means 7, is constituted of a band pass filter in which only the light having a wavelength of the wavelength band (for example, about 350-450 nm) of the second harmonic wave of the second pulsed laser light transmits, and the light having a wavelength other than the wavelength mentioned above is intercepted.

Band pass filters 6 and 7, are arranged so that one of them can be inserted in or removed from an optical path between the dichroic mirror 13 and the vertically illuminated photon detection means 9, and an optical path between the dichroic mirror 30 and the transmitted light detection means 10, respectively. And it is constituted such that when the band pass filter 6 is inserted, the two-photon excitation fluorescence is extracted, and when the band pass filter 7 is inserted, the second harmonic wave is extracted.

The detection means 8, 9, and 10 are constituted of detectors.

Numerical symbol 35 denotes an objective lens.

Performance of the microscope of the first embodiment constituted in this way will be explained. Here, as shown in FIG. 3 for convenience sake, explanation will be made with respect to case that each of the polarizer 32, the polarizer 33, the light analyzer 34 and the half mirror 23 is inserted in a predetermined position on an optical path, respectively, and at the same time, the band pass filter 7 is inserted in an optical path between the dichroic mirror 13 and the vertically illuminated photon detection means 9, and the band pass filter 6 is inserted in an optical path between the dichroic mirror 30 and the transmitted light detection means 10, respectively.

According to the microscope of the first embodiment, pump light which is emanated from the first pulsed laser generating means 1, is polarized to a linear polarized light component of a predetermined direction through the polarizer 32, and it is reflected by the mirror 11 and enters into the half mirror 12. The anti-Stokes light which is emitted from the second pulsed laser generating means 2, is polarized to the linear polarized light having a different angle from that of the pump light through the polarizer 33, and enters into the half mirror 12. The pump light reflected by the half mirror 12 and the Stokes light which transmitted the half mirror 12 are composed as light having passed through the same optical path. Composed light is reflected by the dichroic mirror 13, transmits the dichroic mirror 14, is scanned at light-condensing position of illuminating radiation in the specimen 4 to the direction of two dimensions via Galvanometer mirrors 15 and 16, and is condensed by the objective-lens 17, and then it irradiates a predetermined point in the specimen 4.

The specimen 4 emits the coherent Stokes Raman scattering light by irradiation of the pump light and the anti-Stokes light. The specimen 4 emits the second harmonic wave of the wavelength having a half of the anti-Stokes light by irradiation of the anti-Stokes light. Furthermore, by irradiation of the anti-Stokes light, the specimen 4 generates the two-photon excitation phenomenon, and emits fluorescence at the timing delayed to the coherent Stokes Raman scattering light or the second harmonic wave.

By irradiation light through the irradiation means, among the light which is emitted from the specimen 4 and the light which transmits or the light which is reflected on the specimen 4, the light from the specimen 4 which goes toward the direction where it is reflected enters into the dichroic mirror 14 through the objective lens 17 and galvanometer mirrors 16 and 15. Among the light which entered into the dichroic mirror 14, the coherent Stokes Raman scattering light is reflected with the dichroic mirror 14, and the light having shorter wavelength than that of the coherent Raman scattering light (the pump light, the anti-Stokes light, the two-photon excitation fluorescence, and the second harmonic wave) transmits the dichroic mirror 14, The light which transmitted the dichroic mirror 14 enters into the dichroic mirror 13. Out of the light which entered into the dichroic mirror 13, the light having the wavelength longer than that of the anti-Stokes light (the anti-Stokes light and the pump light) is reflected by the dichroic mirror 13, and light having shorter wavelength than that of the coherent Raman scattering light (the second harmonic wave and the two-photon excitation fluorescence) transmits the dichroic mirror 13.

The light which transmitted the dichroic mirror 13 enters into the band pass filter 7. Among the light which entered into the band pass filter 7, only the second harmonic wave transmits the band pass filter 7, and the light other than the second harmonic wave, (the two-photon excitation fluorescence and the light having other wavelength which transmitted the dichroic mirror 14 very slightly) is intercepted. The second harmonic wave that transmitted the band pass filter 7 is detected by the vertically illuminated photon detection means 9.

By irradiation light through the irradiation means, among the light which is emitted from the specimen 4 and light which transmits or is reflected on the specimen 4, the light from the specimen 4 which goes toward the direction where it transmits enters into the dichroic mirror 30 through the objective lens 35. Among the light which entered into the dichroic mirror 30, the coherent Stokes Raman scattering light is reflected by the dichroic mirror 30, and the light having shorter wavelength than that of the coherent Raman scattering light (the pump light, the anti-Stokes light, the two-photon excitation fluorescence, and the second harmonic wave) transmits the dichroic mirror 30.

The light which transmitted the dichroic mirror 30 enters into the band pass filter 6. Among the light which entered into the band pass filter 6, only the second harmonic wave transmits the band pass filter 7, and the light other than the two-photon excitation fluorescence (the pump light, the anti-Stokes light, the two-photon excitation fluorescence, the second harmonic wave, and other light having a wavelength which transmitted the dichroic mirror 30 very slightly) is intercepted. The two-photon excitation fluorescence that transmitted the band pass filter 6 is detected by the transmitted light detection means 10.

The light reflected by the dichroic mirror 14, is reflected by the mirror 22 and enters into the half mirror 23. The light reflected by the dichroic mirror 30 enters into the half mirror 12. The light reflected by the half mirror 22 and the light which transmitted the half mirror 23, enter into the light analyzer 34. Among the light which entered into the light analyzer 34, the non-resonance scattering light is intercepted by the light analyzer 34, and the coherent Stokes Raman scattering light is reflected with the dichroic mirror 30, and the light having other wavelength which is reflected by the dichroic mirrors 14 and 30 very slightly) passed the light analyzer 34, and enters into the mirror 26 of the spectroscope 24.

The light which entered into the mirror 26 is reflected by the mirror 26 and enters into the spectrum element 27. The light which entered into the spectrum element 27, is dispersed by a predetermined wavelength resolving power, and enters into the distributed projection lens 28, and then its spectrum is projected through the distributed projection lens 28. Among the light of which spectrum projection is carried out, the light having wavelengths other than the coherent Stokes Raman scattering light is intercepted by the shading component 29, and the coherent Stokes Raman scattering light passes the shading component 29, and then it is detected by the detection means 8.

When the band pass filter 6 is inserted in the optical path between the dichroic mirror 13 and the vertically illuminated photon detection means 9, and the band pass filter 7 is inserted in the optical path between the dichroic mirror 30 and the transmitted light detection means 10, the two-photon excitation fluorescence under vertical-illumination is detected by the vertically illuminated photon detection means 9 and the second harmonic wave under transmitted illumination is detected by the transmitted light detection means 10, respectively.

When the half mirror 23 is removed from the optical path, only the F-CSRS light is detected by the detection means 8. When the mirror (symbol is omitted) is used by switching, only the E-CSRS light is detected by the detection means 8.

Thus, according to the microscope of the first embodiment, responding to any object of observation to one specimen by using one microscope, any of the two-photon excitation fluorescence observation, the second harmonic wave observation, and the coherent Raman scattering light observations can be carried out in parallel, or selectively.

In the microscope of the first embodiment, the band pass filters 6 and 7 are constituted so as to enable to be switched, but they can be arranged at any fixed position, respectively. Although the half mirror 23 is constituted so as to enable to be switched through the slider (illustration is omitted), it is constituted such that any one of them can be arranged at a fixed position, or none of them is arranged. Furthermore, it can be constituted such that the polarizer 32, the polarizer 33, and the light analyzer 34 are also arranged at a fixed position, or neither of them is arranged.

Second Embodiment

Figure 5:
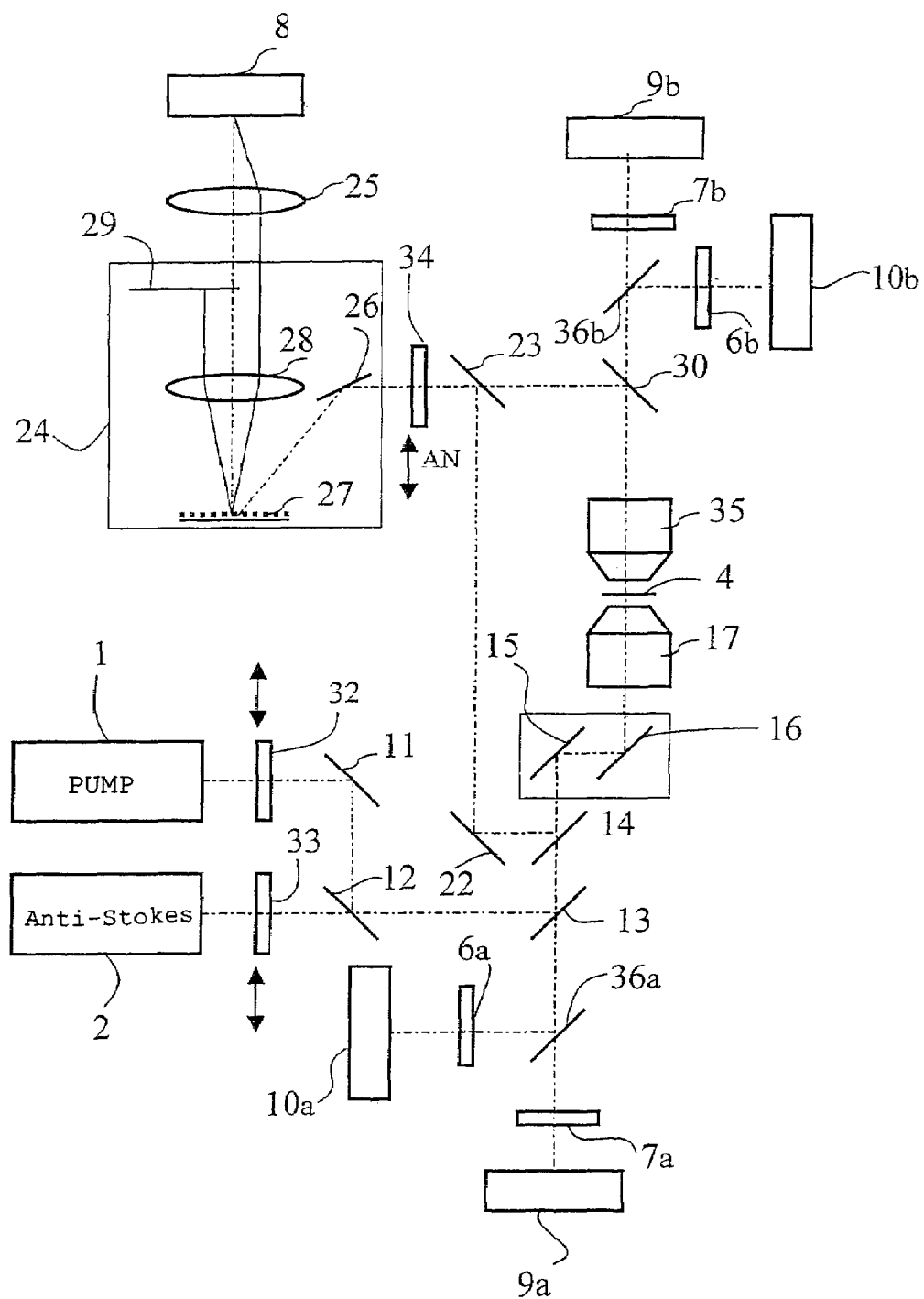
FIG. 5 is a diagram showing an optical composition of the microscope system of the second embodiment according to the present invention.
Figure 6:
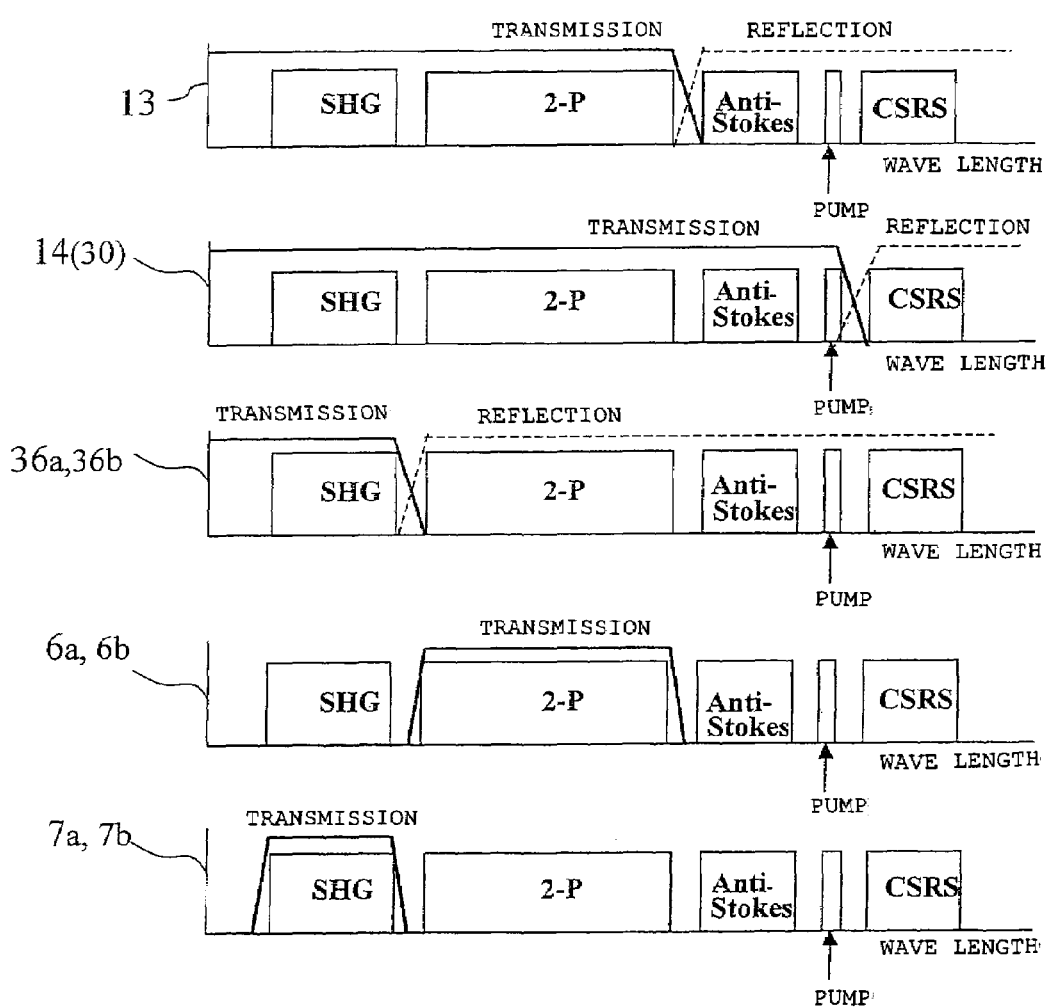
FIG. 6 is a diagrammatic chart showing optical characteristics of a dichroic mirror and a band pass filter used for the microscope in the second embodiment.

FIG. 5 is a diagram showing an outlined composition of the microscope system of the second embodiment according to the present invention. FIG. 6 is a diagrammatic chart showing optical characteristics of a dichroic mirror and a band pass filter used for the microscope in the second embodiment.

In the microscope of the second embodiment, The half mirror 23 is fixed on the optical path where the light reflected by the mirror 22 and the light reflected by the dichroic mirror 30 are crossed, whereby its constitution is limited in such that the coherent Stokes Raman scattering light of both of the F-CSRS light and the E-CSRS light are extracted.

On an optical path at a penetration side of the dichroic mirror 14, a dichroic mirror 36a is arranged. In the dichroic mirror 13, light having a wavelength of the wavelength band (for example, about 350-450 nm) of the second harmonic wave of the second pulsed laser light transmits, and light having a wavelength longer than that of the second harmonic wave is reflected. On an optical path at a penetration side of the dichroic mirror 36a, a band bus filter 7a in which only the light having the wavelength of the wavelength band (for example, about 350-450 nm) of the second harmonic wave of the second pulsed laser light transmits, and the light having the other wavelength is intercepted, and a detector 9a as a vertically illuminated second harmonic wave detection means are arranged. On an optical path at a reflection side of the dichroic mirror 36a, a band pass filter 6a in which only the light having a wavelength of the wavelength band (for example, about 500-650 nm) of the two-photon excitation fluorescence transmits, and the light having a wavelength other than the wavelength mentioned above is intercepted, and a detector 10a as a vertically illuminated two-photon excitation fluorescence detection means are arranged. By such constitution as mentioned above, the vertically illuminated two-photon excitation fluorescence and the vertically illuminated second harmonic wave can be detected in parallel.

On an optical path at penetration side of the dichroic mirror 30, a dichroic mirror 36b having the same optical characteristics as the dichroic mirror 36a is arranged. On an optical path at a penetration side of a dichroic mirror 36b, a band pass filter 7b having the same optical characteristics as the band pass filter 7a, and a detector 9b having the same constitution as the vertically illuminated second harmonic wave detection means 9a as a transmitted second harmonic wave detection means are arranged. On an optical path at a reflection side of the dichroic mirror 36b, a band pass filter 6b having the same optical characteristics as the band pass filter 6a, and a detector 10b having the same constitution as the vertically illuminated second harmonic wave detection means 10a as a forward second harmonic wave detection means are arranged. By such constitution as mentioned above, the forward two-photon excitation fluorescence and the forward second harmonic wave can be detected in parallel.

According to the microscope of the second embodiment, the vertically illuminated second harmonic wave, the vertically illuminated two-photon excitation fluorescence the forward second harmonic wave, the forward two-photon excitation fluorescence, and the coherent Stokes Raman scattering light can be detected at once. Other functions and action effects are almost the same as the microscope of the first embodiment.

Third Embodiment

Figure 7:
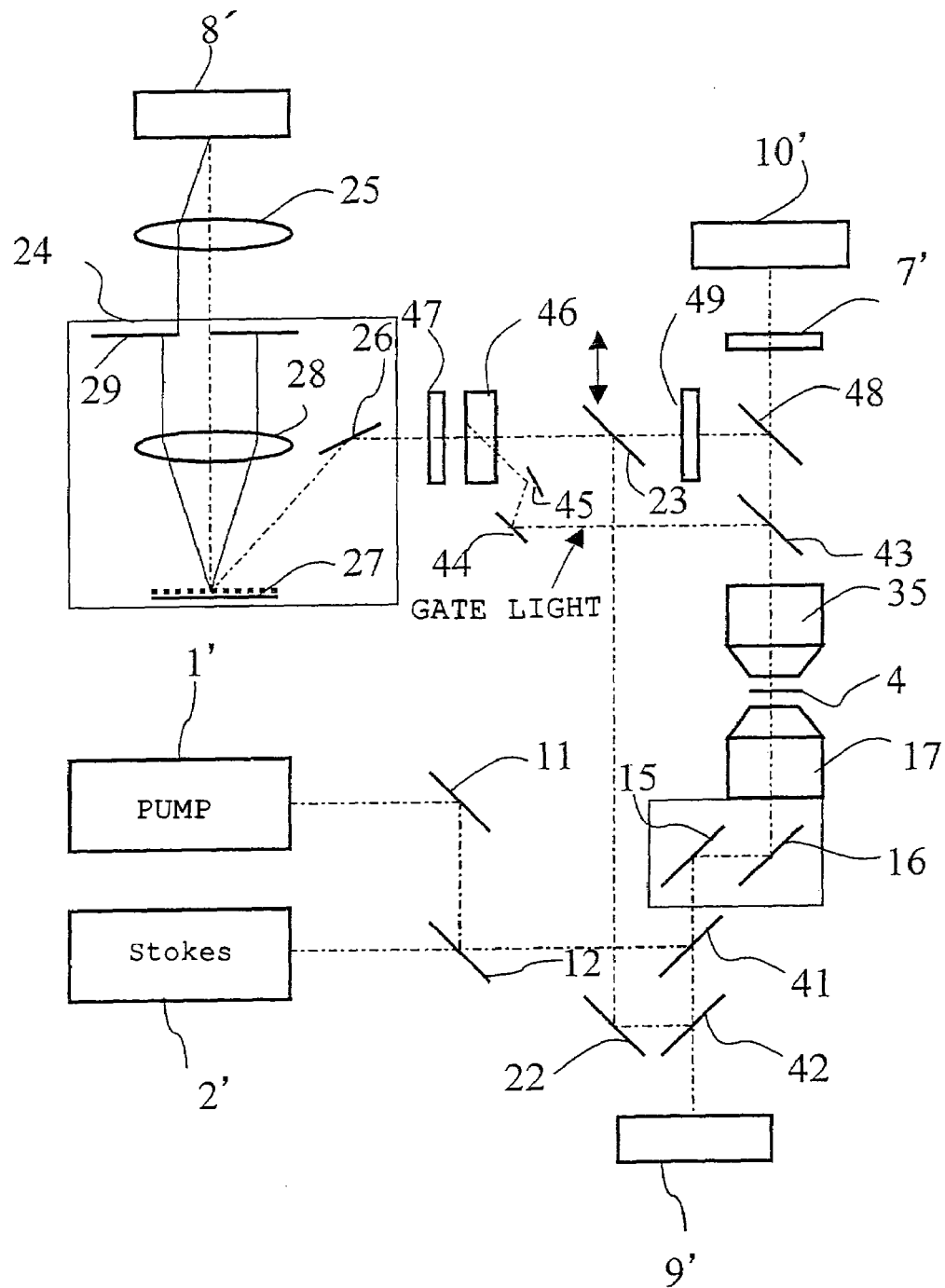
FIG. 7 is a diagram showing an optical composition of the microscope system of the third embodiment according to the present invention.
Figure 8:
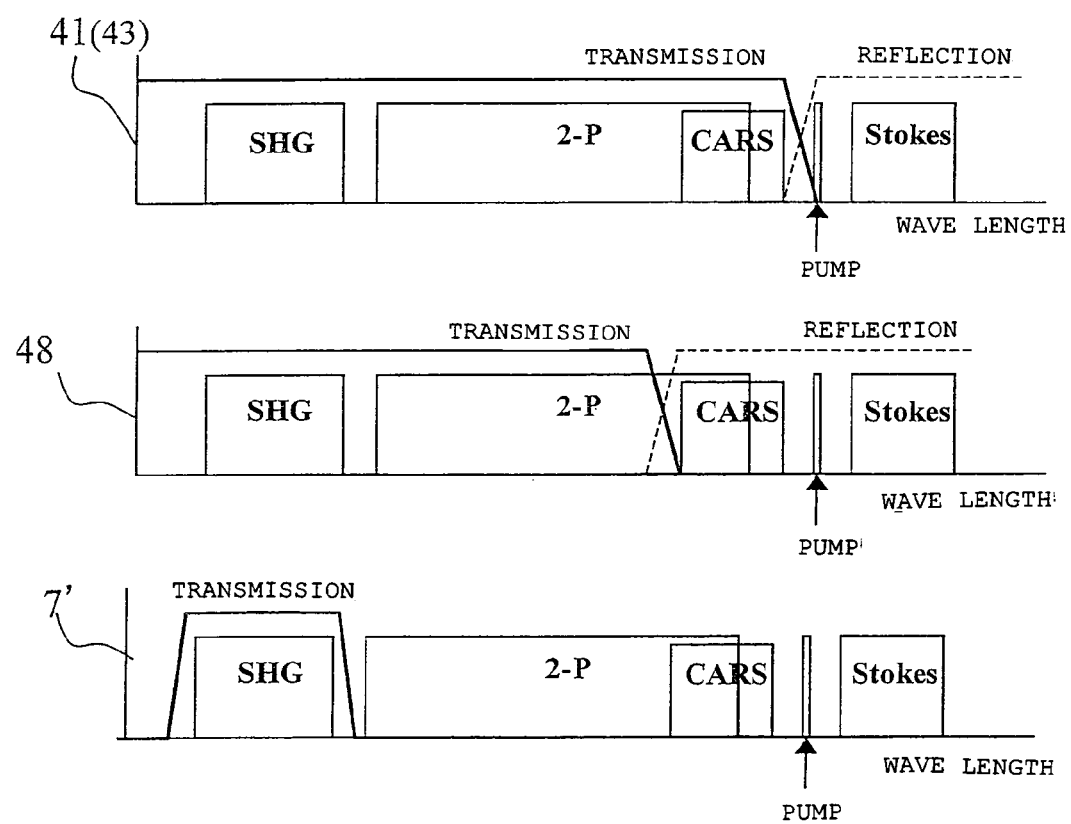
FIG. 8 is a diagrammatic chart showing optical characteristics of a dichroic mirror and a band pass filter used for the microscope in the third embodiment.

FIG. 7 is a diagram showing an outlined composition of the microscope system of the third embodiment according to the present invention. FIG. 8 is a diagrammatic chart showing optical characteristics of a dichroic mirror and a band pass filter used for the microscope in the third embodiment.

The microscope of the third embodiment comprises a first pulsed laser generating means 1' that generates a first pulse light having a first wavelength component, a second pulsed laser generating means 2' that generates a second pulse light having a second wavelength component, an irradiation means (symbol is omitted) which is constituted so that irradiation to the specimen 4 can be carried out by composing the first pulse light and the second pulse light, a coherent anti-Stokes Raman scattering light extraction means (symbol is omitted) which extracts only coherent anti-Stokes Raman scattering light from the light emanated from the specimen 4 to which irradiating light is irradiated through the irradiation means, a vertically illuminated the two-photon excitation fluorescence extraction means (symbol is omitted) which extracts only the two-photon excitation fluorescence generated by irradiating the second pulse light to the specimen 4 from the light emanated from the specimen 4 to which irradiating light is irradiated through the irradiation means (symbol is omitted), a forward second harmonic wave extraction means 7 that extracts only light having the second harmonic wave component generated by irradiating the second pulse light to the specimen 4 from the light from the specimen 4 to which irradiating light is irradiated through the irradiation means, a coherent anti-Stokes Raman scattering light detection means that detects the coherent anti-Stokes Raman scattering light, a vertically illuminated two-photon excitation fluorescence detection means 9' which detects the two-photon excitation fluorescence, and a forward second higher-harmonic-wave-detection-means 10' which detects the second harmonic wave. The first pulsed laser generating means 1', is constituted of a pulsed laser light source which generates pulse light having pulse width of picosecond at wavelength, for example, about 700 nm as the first pulse light.

A second pulsed laser generating means 2' is constituted of a pulsed laser light source which generates pulse light, as the second pulse light, having a pulse width of femtosecond at a wavelength in a predetermined wavelength band (for example, about 700-900 nm) whose wavelength is longer than that of the first pulse light,. The second pulsed laser generating means 2' is constituted such that scan can be carried out by using the wavelength of the second pulse light within the predetermined wavelength band (about 700-900 nm).

In the microscope of the third embodiment, it is constituted such that the first pulse light functions as pump light, and the second pulse light functions as anti-Stokes light. An irradiation means is constituted of the mirror 11, the half mirror 12, the dichroic mirror 41, the galvanometer mirrors 15 and 16, and the objective lens 17. The half mirror 12 is arranged on an optical path where the first pulse light and second pulse light are crossed.

The dichroic mirror 41 has optical characteristics such that light having wavelength shorter than the wavelength band (for example, about 700 nm) of pump light can transmit it, and it reflects the light having a wavelength longer than the wavelength of the pump light.

The galvanometer mirrors 15 and 16 are constituted so that a light-condensing position of illuminating radiation in the specimen 4 may be scanned in the direction of two dimensions.

The coherent anti-Raman scattering light extraction means is constituted of the E-CSRS light extraction means (symbol is omitted) which extracts the coherent anti-Stokes Raman scattering light from the light emanated from the specimen 4 which goes toward the direction in which the light irradiated through the irradiation means is reflected, and the F-CARS light extraction means (symbol is omitted) which extracts the coherent anti-Stokes Raman scattering light from the light emanated from the specimen 4 which goes toward the direction which the light irradiated through the irradiation means transmits.

The F-CARS-light extraction means is constituted of a polarization beam splitter 42, a half mirror 22, a half mirror 23, a dichroic mirror 43, mirrors 44, 45, a Kerr gate 46, a light analyzer 47, a spectroscope 24, and a lens 25. The polarization beam splitter 42 has an optical characteristics such that linear polarized light is reflected, and light other than linear polarized light is reflected or transmits (that is, the transmitted light is restricted to light other than linear polarized light) and it also has a function as a vertically illuminated two-photon excitation fluorescence extraction means which extracts the two-photon excitation fluorescence which is not linear polarized light.

The dichroic mirror 43 has optical characteristics such that light having wavelength shorter than the wavelength band (for example, about 700 nm) of the pump light can transmit it, and it reflects the light having a wavelength longer than the wavelength of the pump light, like the case of the dichroic mirror 43.

The mirror 45 is arranged so that light may be entered slantingly into the Kerr gate 46. The Kerr gate 46 has a function to rotate a polarization direction of the linear polarized light which transmits the half mirror 23 and is reflected on it, and enters into the Kerr gate 46, to a predetermined direction, when light enters slantingly from the mirror 45.

The light analyzer 47 has optical characteristics such that the linear polarized light of which a direction of polarization has been changed when it transmits the Kerr gate 46 can transmit it, and linear polarized light which does not change in polarization direction when it transmits the Kerr gate 46, is intercepted, The spectroscope 24 is constituted of a mirror 26 which leads incidence light to a spectrum element 27, the spectrum element 27 which consists of a grating etc., a distributed projection lens 28 which projects the light distributed by the spectrum element 27, a shading component 29 arranged so that the coherent anti-Stokes Raman scattering light may be passed and the other light may be intercepted.

The F-CARS-light extraction means is constituted of a dichroic mirror 48, a polarizer 49, a half mirror 23, a dichroic mirror 43, mirrors 44, 45, a Kerr gate 46, a light analyzer 47, a spectroscope 24, and a lens 25.

The dichroic mirror 48 has optical characteristics such that light having a wavelength longer than wavelength band (for example, 570-700 nm) of the coherent anti-Stokes Raman scattering light is reflected, and light having shorter wavelength than that of the coherent anti-Raman scattering light transmits it.

The polarizer 49 has optical characteristics which converts the two-photon excitation fluorescence having a random polarization direction into linear polarized light.

The mirror 44 and the mirror 45 have a regulating function such that at the same timing as such timing that the coherent anti-Stokes Raman scattering light (the E-CARS light and F-CARS light) which is reflected at the half mirror 23 and transmitted it enters into the Kerr gate 46, the Stokes light from the mirror 45 is made enter in the Kerr gate 46.

The half mirror 23 is arranged on an optical path where the light reflected by the mirror 22 and the light which transmitted the polarizer 49 are crossed.

The half mirror 23 and another mirror (illustration is omitted) are arranged at a slider (illustration is omitted), and it is constituted so as to switch the following three conditions; that is, the condition mentioned above, a condition where the half mirror 23 has been removed from the optical distance through the slider, and a condition changed by switching from the half mirror 23 to another mirror (illustration is omitted). In FIG. 7, the half mirror 23 is arranged on the optical path, where a condition in which the CARS light of both the E-CARS light and the F-CARS light can be extracted is shown. It is constituted such that when the half mirror 23 is removed from the optical path, only the F-CARS light is extracted, and when the mirror (symbol is omitted) is used by switching, only the E-CARS light is extracted.

In the microscope of the third embodiment, for convenience, illustration has been omitted. However, it is possible to constitute such that as the P-CSRS (POLARIZATION COHERENT ANTI-STOKES RAMAN) light extraction means which extracts polarized type coherent anti-Stokes Raman scattering light, like the P-CSRS light extraction means in the first embodiment, a first polarizer which converts into a predetermined linear polarized light is arranged between the first pulsed laser generating means 1' and the mirror 11, and a second polarizer which converts into a linear polarized light having a different angle from that of the linear polarized lightn which is converted with the first polarizer is arranged between the second pulsed laser generating means 2' and the mirror 12, and a light analyzer in which the linear polarized light of the coherent Anti-Stokes Raman scattering light transmits and the non-resonance scattering light is intercepted is arranged between the half mirror 23 and the spectroscope 24 can be are arranged so that they can be attached and detached via the slider etc., respectively.

If the P-CARS light extraction means is inserted in the optical path, by irradiating to a specimen, the first pulse light and the second pulse light which have been converted into the linear polarized light having different oscillating directions, respectively, and further by extracting only the linear polarized light component of a specific direction from the scattering light, the non-resonant Raman scattering component as background noise is removed. Accordingly, the coherent Anti-Stokes Raman scattering light can be detected with high sensitivity.

The two-photon excitation fluorescence extraction means comprises the beam splitter 42 having the optical characteristics which reflects linear polarized light, and transmits or reflects the light other than linear polarized light, as mentioned above, and the pump light, the Stokes light, the coherent anti-Stokes Raman scattering light, and the second harmonic wave which are linear polarized light are unable to transmit, but only the light having a wavelength of the wavelength band (for example, about 500-650 nm) of the two-photon excitation fluorescence other than linear polarized light is able to transmit.

The second harmonic wave extraction means 7' is constituted such that a band pass filter in which only the light having a wavelength of the wavelength band (for example, about 350-450 nm) of the second harmonic wave of the second pulsed laser light transmits, and the light having a wavelength other than the wavelength mentioned above is intercepted.

As mentioned above, the microscope of the third embodiment comprises as a separation means for separating the coherent anti-Raman scattering light and the two-photon excitation fluorescence, a time-resolved means constituted of a delayed optical system such as mirrors 44, 45 etc., and Kerr-gate 46 etc.

Since a part of wavelength bands of the coherent anti-Stokes Raman scattering light and the two-photon excitation fluorescence may overlap, it is necessary to separate them. However, in the specimen the coherent anti-Stokes Raman scattering light is generated only at the moment when the excitation light pulse which is the Stokes light is irradiated. But, the two-photon excitation fluorescence is generated behind time from irradiation of the excitation light pulse, and light emitting is continued for the time being after the excitation light pulse disappeared. Then, by arranging the Kerr gate 46, a timing at which the excitation light pulse (the Stokes light) and the coherent anti-Stokes Raman scattering light enter into the Kerr gate 46, and a timing at which the two-photon excitation fluorescence enters into the Kerr gate 46 are shifted, polarization directions of the coherent anti-Stokes Raman scattering light and the two-photon excitation fluorescence when they pass the Kerr gate 46, can be made to be different, and accordingly, by separating for every different polarization component, each light can be separated.

Then, performance or action of the microscope of the third embodiment constituted in this way will be explained. Here, a case where the P-CARS light extraction means which is not illustrated is not inserted in the predetermined position on the optical path, and the CARS-light half mirror 23 is inserted in the predetermined position on the optical path will be explained here for convenience sake.

According to the microscope of the third embodiment, the pump light emanated from the pulsed laser generating means 1' is reflected by the mirror 11 and enters into the half mirror 12. The Stokes light emitted from the second pulsed laser generating means 2' enters into the half mirror 12. The pump light reflected by the half mirror 12 and the Stokes light which transmitted the half mirror 12 are compounded as light passing through the same optical path. The composed light is reflected by the dichroic mirror 41, is scanned at light-condensing position of illuminating radiation in the specimen 4 to the direction of two dimensions via the galvanometer mirrors 15 and 16, and is condensed by the objective-lens 17, and then irradiates a predetermined point in the specimen 4.

By irradiating the pump light and the Stokes light to the specimen 4, it emits the coherent anti-Raman scattering light, By irradiating the Stokes light to the specimen 4, it emits the second harmonic wave of the wavelength of a half of the Stokes light. Further, by irradiating the Stokes light to the specimen 4, the two-photon excitation phenomenon is generated, and fluorescence is emitted at delayed timing for the coherent anti-Stokes Raman scattering light or the second harmonic wave.

Among the light which is emitted from the specimen 4 and the light which transmits the specimen 4 or is reflected on it by irradiating the light through the irradiation means, the light from the specimen 4 which goes toward the direction where it is reflected enters into the dichroic mirror 41 through the objective lens 17 and the galvanometer mirrors 16 and 15. Among the light which entered into the dichroic mirror 41, the pump light and the Stokes light are reflected with the dichroic mirror 14. And the light having shorter wavelength than that of the pump light (the coherent anti-Stokes Raman scattering light, the two-photon excitation fluorescence, and the second harmonic wave) transmits the dichroic mirror 41.

The light which transmitted the dichroic mirror 41 enters into the polarization beam splitter 42. Among the light which entered into the polarization beam splitter 42, the coherent anti-Stokes Raman scattering light and the second harmonic wave which are linear polarized light are reflected by the polarization beam splitter 42. Since the two-photon excitation fluorescence has random polarization directions by nature, very small amount of the linear polarized light components are reflected by the beam splitter 42, and almost all the components that are not linear polarized light transmit the polarization beam splitter 42. Thereby, only the two-photon excitation fluorescence is extracted. The two-photon excitation fluorescence which transmitted the polarization beam splitter 42 is detected by the vertical illumination two-photon excitation fluorescence detection means 9'.

Among the light which is emitted from the specimen 4 and light which transmits the specimen 4 or is reflected on it by irradiating the light through the irradiation means, the light from the specimen 4 which goes toward the direction to which it transmits, enters into the dichroic mirror 43 through the objective lens 35. Among the light which entered into the dichroic mirror 43, the pump light and the Stokes light are reflected with the dichroic mirror 43, and the light having shorter wavelength than that of the pump light (the coherent anti-Stokes Raman scattering light, the two-photon excitation fluorescence, and the second harmonic wave) transmits the dichroic mirror 43.

The light which transmitted the dichroic mirror 43 enters into the dichroic mirror 48. Among the light which entered into the dichroic mirror 48, the light having a wavelength longer than wavelength band (for example, 570-700 nm) of the coherent anti-Stokes Raman scattering light (the two-photon excitation fluorescence and the anti-coherent Raman scattering light of which wavelengths overlap mutually in a part of wavelength domains) is reflected by the dichroic mirror, and the light having shorter wavelength than that of the coherent anti-Raman scattering light (the two-photon excitation fluorescence, and the second harmonic wave) transmits the dichroic mirror 48.

The light which transmitted the dichroic mirror 48 enters into the band pass filter 7'. Out of the light which entered into the band pass filter 6, only the second harmonic wave transmits the band pass filter 7, and the lights other than the second harmonic wave (the two-photon excitation fluorescence and the light having other wavelength which transmitted the dichroic mirror 14 very slightly) is intercepted. The second harmonic wave that transmitted the band pass filter 7 is detected by the forward second harmonic wave detection means 10'.

The light reflected by the polarization beam splitter 42, is reflected by the mirror 22 and enters into the half mirror 23. The light reflected by the dichroic mirror 48 transmits a polarizer 49. At this time, the two-photon excitation fluorescence is converted into linear polarized light. The light which transmitted the polarizer 49 enters into the half mirror 23.

The light reflected by the half mirror 22 and light which transmitted the half mirror 23, enter into the Kerr gate 46 at a timing which is different by the Stokes coherent Raman scattering light and the two-photon excitation fluorescence enters into the Kerr gate 46.

At this time, the pump light reflected by the dichroic mirror 43, and the Stokes light enter into the Kerr gate 46 slantingly via the mirrors 44 and 45, by the same timing as the timing by which the Stokes coherent Raman scattering light enters slantingly into the Kerr gate 46. If the Stokes light enters into the Kerr gate 46 slantingly, the polarization direction of the light which transmits the Kerr gate 46 is rotated by the predetermined direction (that is, a polarization direction changes). Accordingly, the coherent anti-Stokes light which entered into the Kerr gate 46 transmits the Kerr gate 46, while the polarization direction is rotated to a predetermined direction.

The coherent anti-Stokes light which transmitted the Kerr gate 46 and has a polarization direction changed, enters into the mirror 26 of the spectroscope 24. The light which entered into the mirror 26 is reflected by the mirror 26 and enters into the spectrum element 27.

The light which entered into the mirror 26 is reflected by the mirror 26 and enters into the spectrum element 27. The light which entered into the spectrum element 27 is dispersed by a predetermined wavelength resolving power, and enters into the distributed projection lens 28, and then its spectrum is projected through the distributed projection lens 28. Among the light of which spectrum projection is carried out, the light having a wavelength other than that of the coherent anti-Stokes Raman scattering light is intercepted by the shading component 29, and the coherent anti-Stokes Raman scattering light passes the shading component 29, and then it is detected by the detection means 8.

On the other hand, a timing at which the two-photon excitation fluorescence enters into the Kerr gate 46 at different timing from the coherent anti-Stokes Raman scattering light is shifted from the timing at which the Stokes light enters slantingly into the Kerr gate 46.

Therefore, the two-photon excitation fluorescence which entered into the Kerr gate 46, transmits the Kerr gate 46 without rotating the polarization direction.

The two-photon excitation fluorescence which does not change the polarization direction even when it transmits the Kerr gate 46 is intercepted by the light analyzer 47. For this reason, the two-photon excitation fluorescence does not reach the detector 9'.

By this, the coherent anti-Stokes Raman scattering light and the two-photon excitation fluorescence can be separated, extracted and detected.

When the half mirror 23 is removed from the optical path, only the F-CARS light is detected by the detection means 8', and when the mirror (illustration is omitted) is used by switching, only the E-CARS light is detected by the detection means 8'.

Therefore, according to the microscope of the third embodiment, by using single microscope to one specimen, responding to a purpose of observation, the two-photon excitation fluorescence observation, the second harmonic wave observation, and the coherent anti-Stokes Raman scattering light observation can be carried out in parallel, or selectively.

In the microscope of the embodiment 3, it is constituted such that the two-photon excitation fluorescence may be detected by the vertically illuminated light and the second harmonic wave may be detected by the penetration light. However, it is not limited to such constitution, and it is possible to constitute so that two-photon excitation fluorescence may be detected by the penetration light and the second harmonic wave may be detected by the vertically illuminated light.

Also in case where multiphoton excitation fluorescence such as three or more photons are generated, by carrying out the time dissolved processing as shown in the embodiment, the multiphoton excitation fluorescence and the second harmonic wave can be separated and detected.

Fourth Embodiment

Figure 9:
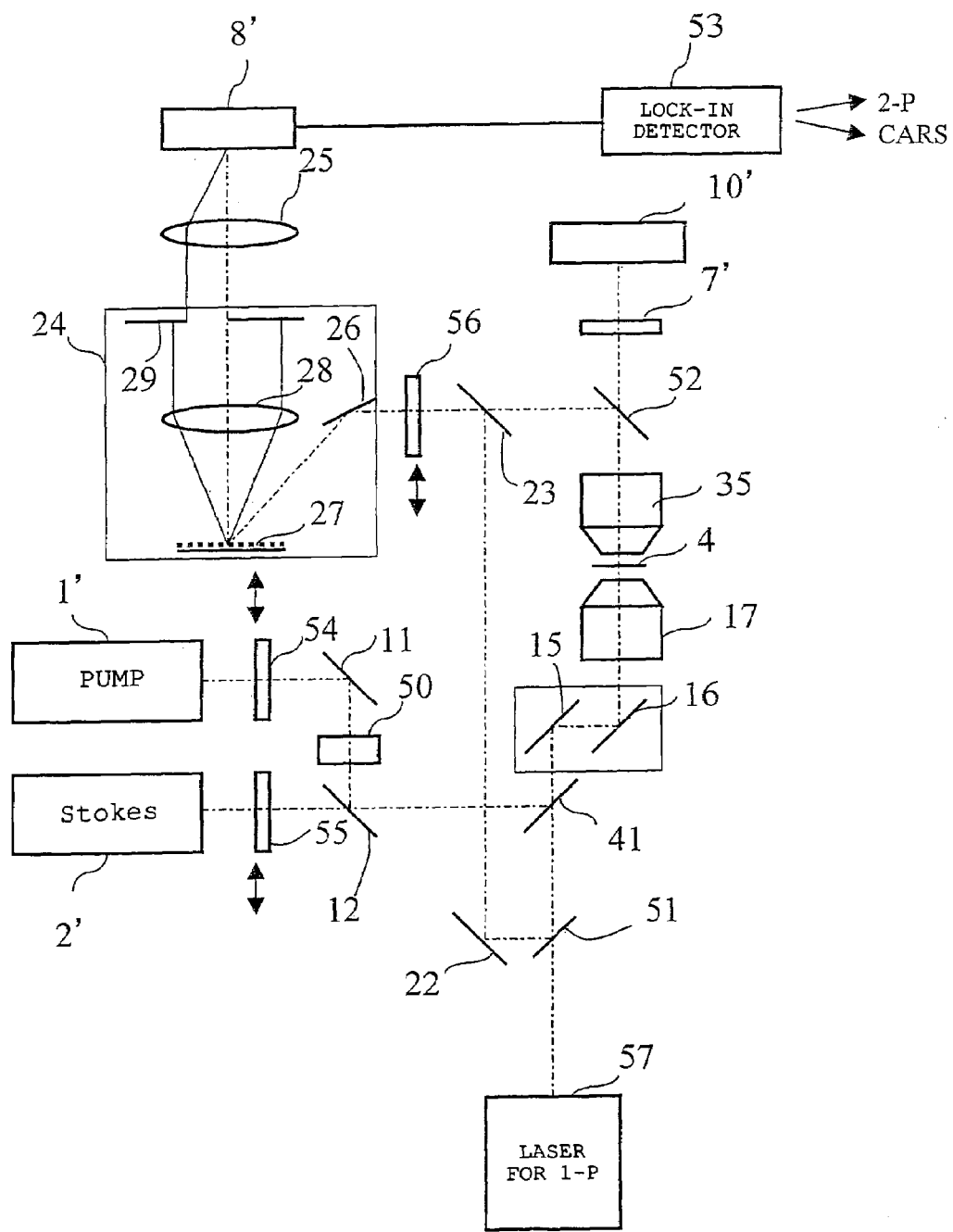
FIG. 9 is a diagram showing an optical composition of the microscope system of the fourth embodiment according to the present invention.
Figure 10:
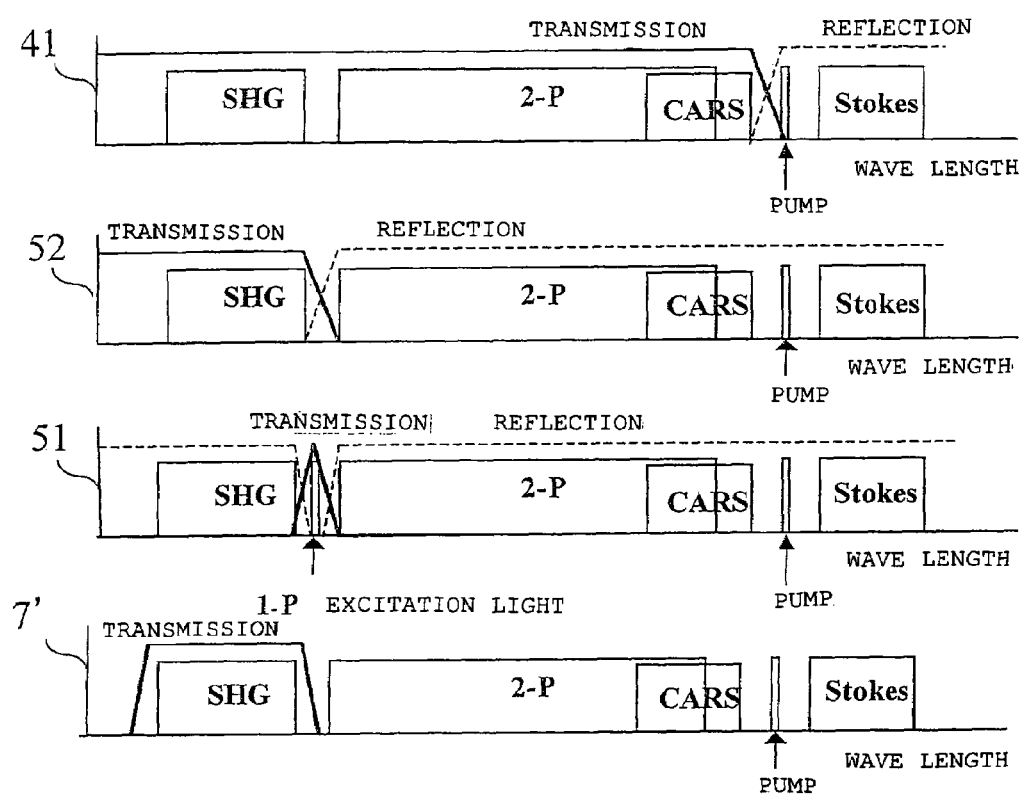
FIG. 10 is a diagrammatic chart showing optical characteristics of a dichroic mirror and a band pass filter used for the microscope in the fourth embodiment.

FIG. 9 is a diagram showing an outlined composition of the microscope system of the fourth embodiment according to the present invention. FIG. 10 is a diagrammatic chart showing optical characteristics of a dichroic mirror and a band pass filter used for the microscope in the fourth embodiment.

Also the microscope of the fourth embodiment, like the microscope of the third embodiment, is constituted as a microscope which detects the second harmonic wave, the two-photon excitation fluorescence, and the coherent anti-Stokes Raman scattering light.

The microscope of the fourth embodiment comprises a modulator 50, as a means for separating the coherent anti-Stokes Raman scattering light and the two-photon excitation fluorescence, and as a modulation means which generates the coherent anti-Stokes Raman scattering light in modulated state, and a lock-in detector 53 as a detection means, which serves both as the coherent anti-Stokes Raman scattering photon detection means and the two-photon excitation fluorescence detection means, and receives both of the modulated coherent anti-Stokes Raman scattering lights and the two-photon excitation fluorescence, and separates and detects a modulated component and a non-modulated component from received light.

Here, for convenience, different points from the constitution of the microscope of the third embodiment will be explained. The same mark is attached to an optical element having the same constitution in the third embodiment, and explanation of the same constitution will be omitted.

A modulator 50 is constituted by using AOM (acoustic-optical modulation element) or EOM (electro-optical modulation element) which is arranged on an optical path between the mirror 11 and the half mirror 12.

A lock-in detector 53 which is connected to the detector 8', has a function such that among signals received by the detector 8', AC component modulated, and DC component to which modulation has not been applied is separated and detected.

In the microscope of the fourth embodiment, the dichroic mirror 43, the mirrors 44 and 45, the polarizer 49, the Kerr gate 46, the light detector 47, and the detector 9' in the microscope which are arranged at the third embodiment 3 are not provided, and in stead of the polarization beam splitter 42 and the dichroic mirror 48 in the microscope of the third embodiment, dichroic mirrors 51 and 52 are arranged. The dichroic mirror 51 has optical characteristics that transmits only the light having a wavelength (for example, about 500 nm) of single photon excitation light, and reflects the lights having other wavelength bands including the coherent anti-Stokes light and the two-photon excitation fluorescence. The dichroic mirror 52 has optical characteristics that transmits the light having a wavelength of the wavelength band (for example, about 350-450 nm) of the second harmonic wave of the second pulsed laser light and reflects the light having a wavelength longer than that of the second harmonic wave.

In the microscope of the fourth embodiment, it is constituted such that the spectroscope 24 intercepts, by the shading component 29, the light having a wavelength other than the coherent anti-Stokes Raman scattering light and the two-photon excitation fluorescence among the light which projects spectrum through the distributed projection lens 28, and the coherent anti-Stokes Raman scattering light and the two-photon excitation fluorescence may pass the shading component 29. Further, it is constituted such that the coherent anti-Stokes Raman scattering light and the two-photon excitation fluorescence are received together by the detector 8'.

In the microscope of the fourth embodiment, as similar to the P-CSRS light extraction means in the first embodiment, as the P-CARS (POLARIZATION COHERENT ANTI-STOKES RAMAN) light extraction means which extracts polarized type coherent anti-Stokes Raman scattering light, a polarizer 54 for converting into a predetermined linear polarized light is arranged between the first pulsed laser generating means 1' and the mirror 11, and a polarizer 55 converted into the linear polarized light which has different angle from that of the linear polarized light converted with the polarizer 54 is arranged between the second pulsed laser generating means 2' and the half mirror 12, and between the half mirror 23 and the spectroscope 24, a light detector 56 in which the linear polarized light of the coherent anti-Stokes Raman scattering light transmits, and the non-resonance scattering light is intercepted is arranged, where they can be attached or detached via the slider, etc., respectively.

Further, in the microscope of the fourth embodiment, it is constituted that at the incidence side of the optical path of the dichroic mirror 51 the laser light source for the single photon excitation 57 is arranged, and normal single photon excitation fluorescence can be also detected through the lock-in detector 53. Naturally, it can be constituted such that the laser light source for the single photon excitation 57 is not arranged.

Then, performance or action of the microscope of the fourth embodiment constituted in this way will be -explained. Here, for convenience, a case where the polarizer 54, the polarizer 55, the light analyzer 56, and the half mirror 23 are inserted in a predetermined position of an optical path will be explained.

According to the microscope of the fourth embodiment, the pump light emanated from the pulsed laser generating means 1' is polarized to a linear polarized light component of a predetermined direction through the polarizer 54, and then it is reflected by the mirror 11 and enters into the modulator 50, and then it is modulated through the modulator 50 and enters into the half mirror 12. The Stokes light emitted from the second pulsed laser generating means 2' is polarized to the linear polarized light having different angle from the pump light through the second polarizer 55, and enters into the half mirror 12. The modulated pump light reflected by the half mirror 12, and the Stokes light which transmitted the half mirror 12 are composed as light which passes on the same optical path. The composed light is reflected by the dichroic mirror 41, and is scanned at light-condensing position of illuminating radiation in the specimen 4 to the direction of two dimensions via the galvanometer mirrors 15 and 16, and then it is condensed by the objective-lens 17, and irradiates a predetermined portion on the specimen 4.

The specimen 4 emits the coherent anti-Stokes Raman scattering light as the pump light and the Stokes light are irradiated. By irradiating the Stokes light being, the specimen 4 emits the second harmonic wave having a wavelength of a half of the Stokes light. Furthermore, by radiating the Stokes light to the specimen 4, the two-photon excitation phenomenon is generated, and fluorescence is emitted at delayed timing for the coherent anti-Stokes Raman scattering light or the second harmonic wave. At this time, since the pump light is modulated, the generated coherent Stokes Raman scattering light is modulated. On the other hand, since the Stokes light has not been modulated, modulation does not start in the second harmonic wave and the two-photon excitation fluorescence of the Stokes light generated.

Among the light emitted from the specimen 4 by irradiating light through the irradiation means, and the light which transmits the specimen 4 and is reflected by it, the light from the specimen 4 which goes toward the direction in which it is reflected, passes the objective lens 17 and the galvanometers mirrors 16 and 15, and then it enters into the dichroic mirror 41. Among the light which entered into the dichroic mirror 41, the pump light and the Stokes light are reflected by the dichroic mirror 41, and the light having shorter wavelength than that of the pump light (the coherent anti-Stokes Raman scattering light, the two-photon excitation fluorescence, and the second harmonic wave) transmit the dichroic mirror 41.

The light which transmitted the dichroic mirror 41 enters into the dichroic mirror 51. Among the light which entered into the dichroic mirror 51, the coherent anti-Stokes Raman scattering light, the two-photon excitation fluorescence, and the second harmonic wave are reflected by the dichroic mirror 51, and then they are reflected by the mirror 22 and enter into the half mirror 23.

Among the light which transmits the specimen 4 or reflects by it, and the light which are emitted from a specimen 4 by irradiating light through the irradiation means 3, the light from the specimen 4 which goes toward the direction to which it transmits, enters into the dichroic mirror 52 through the objective lens 35. Among the light which entered into the dichroic mirror 52, the light having a wavelength of the wavelength zone (for example, about 350-450 nm) of the second harmonic wave of the second pulsed laser light transmits the dichroic mirror 52, and the light (the two-photon excitation fluorescence, the coherent anti-Stokes Raman scattering light, the pump light, and the Stokes light) having a wavelength longer than that of the second harmonic wave is reflected by the dichroic mirror 52.

The light which transmitted the dichroic mirror 52 enters into band path filter 7'. Among the light which entered into the band pass filter 6, only the second harmonic wave transmits the band pass filter 7, and the light other than the second harmonic wave having a wavelength of others which transmitted very slightly the dichroic mirror 52 is intercepted. The second harmonic wave which transmitted the band pass filter 7 is detected by the forward second harmonic wave detection means 10'.

The light reflected by the dichroic mirror 52 enters into the half mirror 23. The light reflected by the half mirror 22 and the light which transmitted the half mirror 23, enter into the light analyzer 56. Among the light which entered into the light analyzer 56, the non-resonance scattering light is intercepted by the light analyzer 56, and other light (the two-photon excitation fluorescence, the coherent anti-Stokes Raman scattering light, the pump light, and the Stokes light) passes the light detector 56, and then it enters into the mirror 26 of the spectroscope 24.

The light which entered into the mirror 26 is reflected by the mirror 26 and enters into the spectrum element 27. The light which entered into the spectrum element 27 is dispersed by a predetermined wavelength resolving power, and enters into the distributed projection lens 28, and then its spectrum is projected through the distributed projection lens 28. Among the light of which spectrum is projected, The coherent anti-Stokes Raman scattering light and the light having a wavelength other than that of the two-photon excitation fluorescence are intercepted by the shading component 29, and the coherent Stokes Raman scattering light and the two-photon excitation fluorescence pass the shading component 29, and then they are received together by the detection means 8'. At this time, among the light received by the detection means 8', the coherent anti-Stokes Raman scattering light is modulated, but the two-photon excitation fluorescence has not been modulated.

The signal received by the detection means 8', is converted photo-electrically, and then it is sent to the lock-in detector 53. The signal sent to the lock-in detector 53, is separated to the signal of an AC component which has been modulated and the signal of DC component which has not been modulated, and then they are detected. Thereby, the modulated coherent anti-Stokes Raman scattering light and the two-photon excitation fluorescence to which modulation is not applied, are separated, extracted, and detected, respectively.

When the half mirror 23 is removed from the optical path, only the F-CARS light is detected by the detection means 8'. When the Mirror (symbol is omitted) is used by switching, only the E-CARS light is detected by the detection means 8'.

Thus, according to the microscope of the fourth embodiment, responding to an observation purpose to one specimen, by using single microscope, the two-photon excitation fluorescence observation, the second harmonic wave observation, and the coherent anti-Stokes Raman scattering light observation can be carried out in parallel, or selectively.

The microscope of the fourth embodiment, although it constituted so that a second harmonic wave may be detected by penetration light, it is not limited to such composition, and of course, it is also possible to constitute so that the second harmonic wave may be detected by vertically illuminated light.

Further, in the microscope of the fourth embodiment, when single photon excitation fluorescence is detected, it is constituted that the laser pulse having a predetermined wavelength (about 500 nm) is emitted from the laser light source 57 for single photon excitation. The excitation light emitted from the laser light source 57 for single photon excitation passes the dichroic mirror 51, the dichroic mirror 41, the galvanometer mirrors 15 and 16, and the objective lens 17, and then it irradiates the specimen 4. The single photon excitation fluorescence emitted from the specimen 4 follows the same optical path as the optical path of the two-photon excitation fluorescence, and is received by the detection means 8', and then it is detected by the lock-in detector 53.

Thus, according to the microscope of the fourth embodiment, besides the effects mentioned above, the scope of uses of observation becomes broader, since the single photon excitation fluorescence can be detected too.

In the microscope of the fourth embodiment, the detection means 8' may be constituted of PMT (Photo Multiplier Tube) having one channel, but it may be also constituted by using a multi-channel detector which consists of PMT array or CCD array. If the multi-channel detector is used, spectral dissolution can be carried out about each of the two-photon excitation fluorescence and the coherent anti-Stokes Raman scattering light. Accordingly, component of an irradiated object detected can be analyzed from the dissolved spectrum.

Fifth Embodiment

Figure 11:
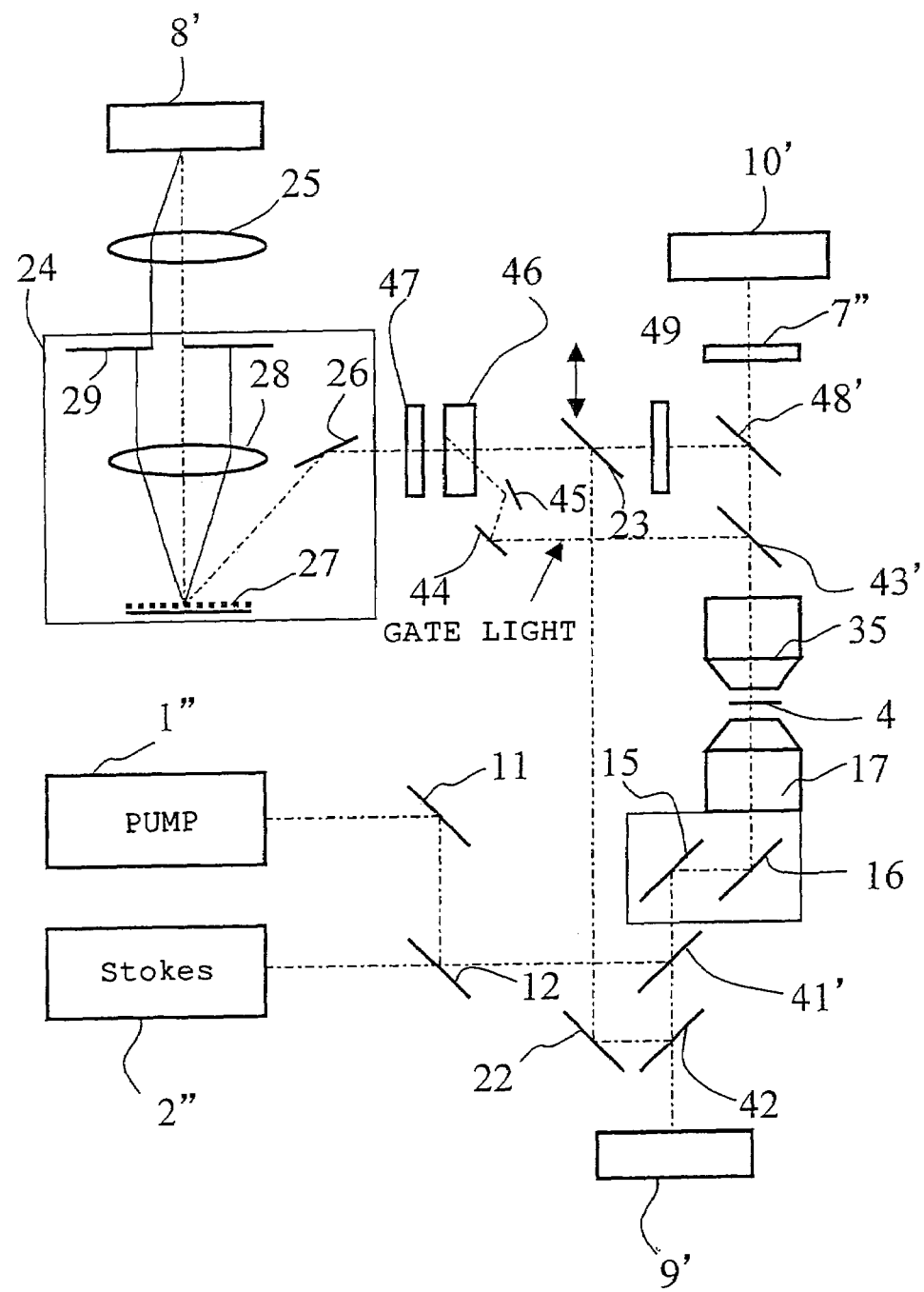
FIG. 11 is a diagram showing an optical composition of the microscope system of the fifth embodiment according to the present invention.
Figure 12:
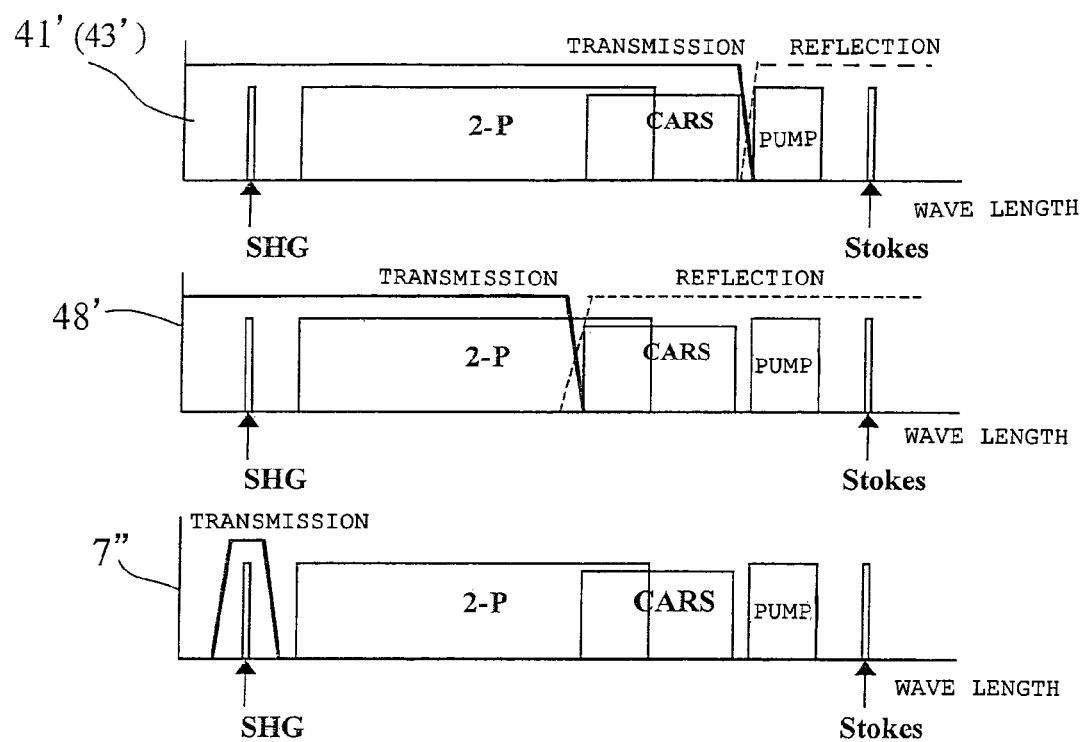
FIG. 12 is a diagrammatic chart showing optical characteristics of a dichroic mirror and a band pass filter used for the microscope in the fifth embodiment.

FIG. 11 is a diagram showing an optical composition of the microscope system of the fifth embodiment according to the present invention. FIG. 12 is a diagram showing an optical characteristics in diagrammatic chart of a dichroic mirror and a band path filter.

Fundamental arrangement constitution of the optical component of the microscope of the fifth embodiment is the same as that of the microscope of the embodiment 3, but the wavelength of the pulse light emitted from the pulsed laser generating means, and the optical characteristics of the dichroic mirror, the band path filter, etc. differ.

In the microscope of the fifth embodiment, the first pulsed laser generating means 1" is constituted of a pulsed laser light source which generates pulse light, as the first pulse light, which has a wavelength of a predetermined wavelength zone (for example, about 700-800 nm) shorter than the wavelength of the second pulse light, and a pulse width of picosecond. The first pulsed laser generating means 1" is constituted such that scanning can be carried out by the wavelength of the first pulse light within the predetermined wavelength zone (about 700-800 nm) mentioned above.

The second pulsed laser generating means 2" is constituted of a pulsed laser light source which generates pulse light, as the second pulse light, which has a wavelength of a predetermined wavelength (about 900 nm) longer than the wavelength of the first pulse light, and a pulse width of femtosecond.

The dichroic mirrors 41' and 43' have optical characteristics that light having a wavelength shorter than the wavelength zone (about 700-800 nm) of the pump light transmits the dichroic mirrors 41' and 43', and light having a wavelength longer than the wavelength zone of the pump light is reflected.

The dichroic mirror 48' has optical characteristics that light having the wavelength longer than the wavelength zone of the coherent anti-Stokes Raman scattering light which is different from the wavelength zone generated in the fifth embodiment is reflected, and light having a wavelength shorter than the wavelength zone of the coherent anti-Stokes Raman scattering light transmits the dichroic mirror 48'.

The second harmonic wave extraction means 7" is constituted of a band path filter in which only the light having a wavelength of the wavelength zone (about 450 nm) of the second harmonic wave of the second pulsed laser light transmits it, and light having the other wavelength is intercepted.

In the microscope of the present invention, the Stokes light is the excitation light in the two-photon excitation fluorescence observation and in the second harmonic wave observation. When scanning is carried out by the wavelength of the Stokes light, since absorption spectrum changes, luminous efficiency of fluorescence changes. Therefore, the two-photon excitation fluorescence and the second harmonic wave cannot be observed while keeping the optimal luminous efficiency.

However, according to the microscope of the fifth embodiment, since it is constituted such that scanning is carried out by the wavelength of the pump light and the wavelength of the Stokes light is fixed, the luminous efficiency of the two-photon excitation fluorescence does not change during scanning by the wavelength of the pump light. Therefore, if a wavelength by which the luminous efficiency of the two-photon excitation fluorescence or the second harmonic wave becomes the optimal is used as Stokes light, the coherent anti-Stokes Raman scattering light can be detected, while detecting the two-photon excitation fluorescence or the second harmonic wave at the optimal emission state.

Sixth Embodiment

Figure 13:
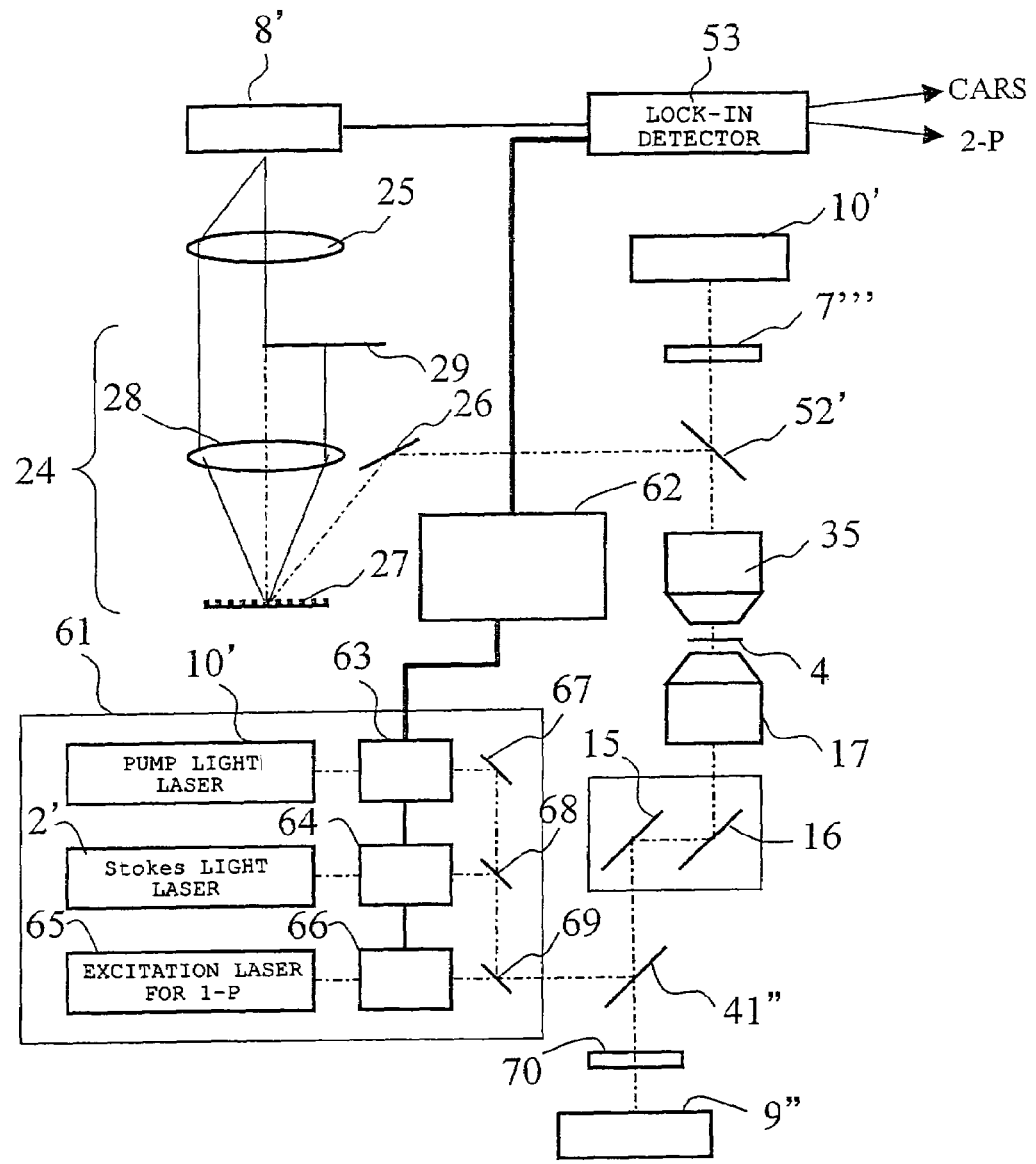
FIG. 13 is a diagram showing an optical composition of the microscope system of the sixth embodiment according to the present invention.
Figure 14:
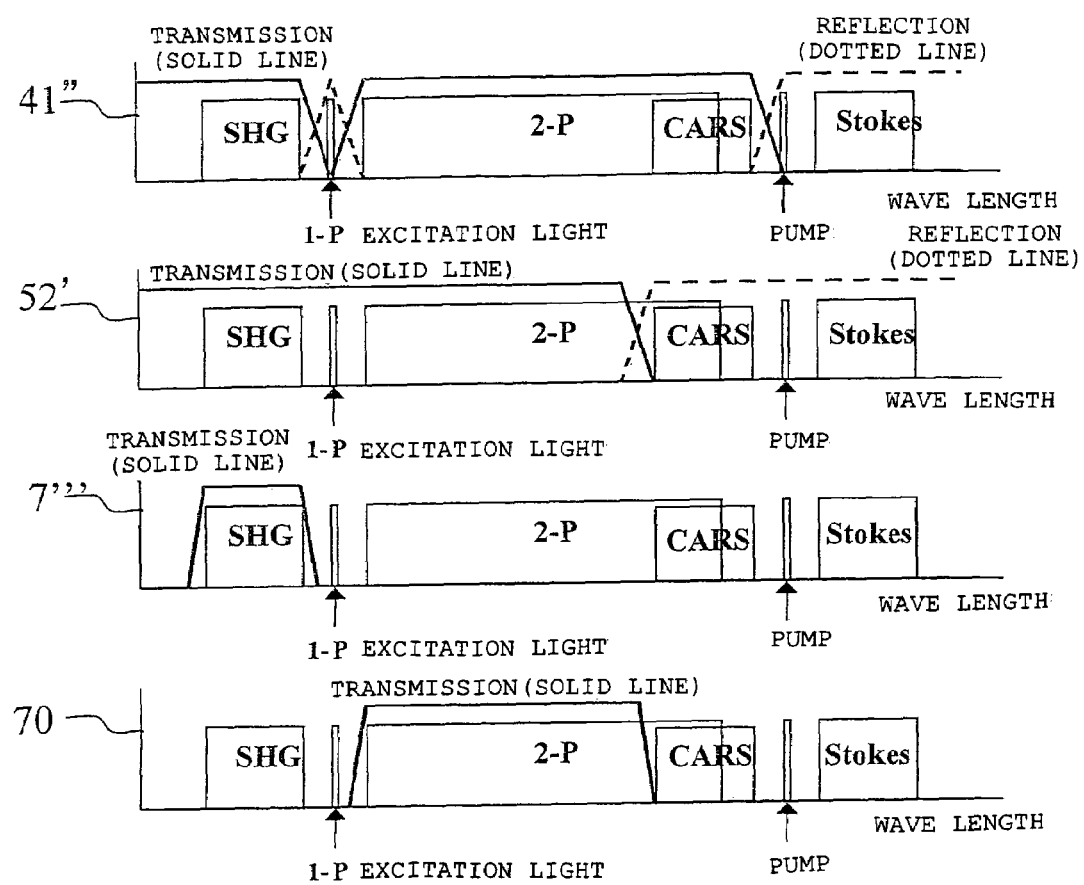
FIG. 14 is a diagrammatic chart showing optical characteristics of a dichroic mirror and a band pass filter used for the microscope in the sixth embodiment.

FIG. 13 is a diagram showing an outlined composition of the microscope system of the sixth embodiment according to the present invention. FIG. 14 is a diagrammatic chart showing optical characteristics of a dichroic mirror and a band path filter used for the microscope of the sixth embodiment, The microscope of the sixth embodiment is constituted such that a laser combiner 61 as a laser light selection means, and a controller 62 as a control means are arranged in the irradiation means of the microscope of the fourth embodiment shown in FIGS. 9 and 10, and the observation technique can be changed by selecting the laser light responding to the area of interest of observation object, A laser combiner 61 comprises a first pulsed laser generating means (pump light generating means) 1', an acoustic optical element 63 which has a function as a switching means which switches ON/OFF of the first pulsed laser generating means 1', and also a function as a modulation means (modulator 50 in the microscope of the fourth embodiment shown in FIG. 9) which modulates the first pulsed laser, a second pulsed laser generating means (Stokes light generating means) 2', an acoustic optical element 64 which is a switching means for switching ON/OFF of the second pulsed laser generating means 2', a pulsed laser generating means 65 for single photon excitation, a acoustic optical element 66 which is a switching means which switches ON/OFF of the pulsed laser generating means 65 for the single photon excitation, a mirror 67 as a composite means for composing the optical paths of such pulsed laser, and half mirrors 68 and 69.

A controller 62 is connected to acoustic optical elements 63, 64, and 66 of the laser combiner 61, and has a function which controls ON/OFF by the acoustic optical elements 63, 64, and 66. Furthermore, the controller 62 is connected to a lock-in detector 53 and has a function to control to switch ON of wavelength separation by the lock-in detector 53 synchronously when switching ON of both the acoustic optical elements 63 and 63, and, also it has a function to control to switch OFF of the lock-in detector 53 in other cases.

In the microscope of the sixth embodiment, it is constituted that the laser combiner 61 is equipped with the pulsed laser generating means 65 for the single photon excitation. However, it can be constituted without having the pulsed laser generating means 65.

In FIG. 13, for convenience of explanation, the mirror 22a, the half mirror 23, the polarizers 54 and 55, and the light detector 56 in the microscope of the fourth embodiment shown in FIG. 9 have been omitted, and the coherent Raman scattering light shows a state where only the F-CARS light is detectable. As a matter of course, it is possible to constitute so that the E-CARS light and P-CARS light can be detected also in the microscope of the sixth embodiment.

The microscope of the sixth embodiment comprises, dichroic mirrors 41" and 52', and the band path filter 7'" having optical characteristics different from those mentioned above are arranged in stead of the dichroic mirrors 41 and 52, and the band path filter 7' in the microscope of the fourth embodiment shown in FIGS. 9 and 10. And on the optical path at penetration side of the dichroic mirror 41", a band path filter 70 for extracting only the two-photon excitation fluorescence of the wavelength zone in which the wavelength does not overlap with that of the coherent anti-Stokes Raman scattering light, and a two-photon excitation fluorescence portion detection means 9'" is arranged in stead of the dichroic mirror 51 and the laser generating means 57 for single photons in the microscope of the fourth embodiment shown in FIGS. 9 and 10.

The dichroic mirror 41" has optical characteristics that the second harmonic wave, the two-photon excitation fluorescence, and the coherent anti-Stokes Raman scattering light transmit it, and the light having the wavelength longer than the wavelength of the single photon excitation light and the wavelength of the pump light are reflected.

The dichroic mirror 52' has optical characteristics that the light having a wavelength shorter than the coherent anti-Stokes Raman scattering light transmits it, and the light having the wavelength longer than the coherent anti-Stokes Raman scattering light is reflected.

The band path filter 7'" has optical characteristics that only the light having the wavelength zone of the second harmonic wave transmits it, and the light having the other wavelength is intercepted.

The band path filter 70 has optical characteristics that only the two-photon excitation fluorescence of the wavelength zone which does not overlap with the coherent anti-Stokes Raman scattering light transmits it, and the light having the other wavelength is intercepted.

Other constitution is almost the same as the microscope of the fourth embodiment.

According to the microscope of the sixth embodiment constituted in this way, observation techniques can be changed according to the area of interest of an object of observation.

For example, when observations by the second harmonic wave, the two-photon excitation fluorescence, and the coherent Raman scattering light are carried out in parallel, the first pulsed laser generating means (the pump light generating means) 1' and the second pulsed laser generating means (the Stokes light generating means) 2' are turned ON, and at the same time, the pulsed laser generating means 65 for the single photon excitation is turned OFF and the lock-in detector 53 is turned ON, via controller 62 and the acoustic optical elements 63, 64, and 65.

Then, the pump light is modulated and emitted from the first pulsed laser generating means 1', and it is reflected by a mirror 67, and then it enters into the half mirror 68. At the same time, the Stokes light is emitted from the second pulsed laser generating means, and enters into the half mirror 68. The pump light which transmitted the half mirror 68, and the Stokes light which transmitted the half mirror 68 are composed as light which passes along the same optical path. Then, through the mirror 69, the dichroic mirror 41", the galvanometer mirrors 15 and 16, and the objective lens 17, the composed light irradiates a predetermined portion on the specimen 4.

The specimen 4 emits the coherent anti-Raman scattering light by irradiating the pump light and the Stokes light to the specimen 4. Further, the specimen 4 emits the second harmonic wave having a wavelength of a half of the Stokes light by being irradiated by the Stokes light. Furthermore, by being irradiated by the Stokes light, the specimen 4 generates the two-photon excitation phenomenon, and emits fluorescence at the timing which was delayed to the coherent anti-Stokes Raman scattering light or the second harmonic wave. At this time, since the pump light is modulated, the generated coherent Stokes Raman scattering light is also modulated. On the other hand, since the Stokes light has not been modulated, the second harmonic wave and the two-photon excitation fluorescence of the Stokes light which are generated are also not modulated.

Among the light which is emitted from the specimen 4 by being irradiated by the illuminating light, and the light which transmits the specimen 4 or is reflected on it, the light from the specimen 4 which goes toward the direction in which it is reflected enters into the dichroic mirror 41." via the objective lens 17 and the galvanometers mirrors 16 and 15.

Among the light which entered into the dichroic mirror 41", the second harmonic wave, the two-photon excitation fluorescence, and the coherent anti-Stokes Raman scattering light transmit the dichroic mirror 41", and the light having a wavelength longer than the wavelength of the pump light is reflected by the dichroic mirror 41". The light which transmitted the dichroic mirror 41" enters into the band path filter 70. Among the light which entered into the band path filter 70, only the two-photon excitation fluorescence having a wavelength zone which does not overlap with that of the coherent anti-Stokes Raman scattering light transmits the band path filter 70, and the light having other wavelengths is intercepted by the band path filter 70. The light which transmitted the band path filter 70 is detected by the detection means 9." Thereby, The two-photon excitation fluorescence having the wavelength zone which does not overlap with the coherent anti-Stokes Raman scattering light can be detected.

Among the light which is emitted from the specimen 4 irradiated by the illuminating light and the light which transmits the specimen 4 or is reflected on it, the light from the specimen 4 which goes toward the direction to which it transmits passes through the objective lens 35 and enters into the dichroic mirror 52'. Among the light which entered into dichroic mirror 52', the light having a wavelength shorter than the coherent anti-Stokes Raman scattering light transmits the dichroic mirror 52', and the light having a wavelength longer than the coherent anti-Stokes Raman scattering light is reflected by the dichroic mirror 52'.

The light which transmitted the dichroic mirror 52' enters into the band path filter 7'''. Among the light which entered into the band path filter 7''', only the light having a wavelength zone of the second harmonic wave transmits the band path filter 7''', and the light having the other wavelength is intercepted by the band path filter 7'''. The second harmonic wave which transmitted the band path filter 7''' is detected by the detector 10'.

The light reflected by the dichroic mirror 52' enters into the mirror 26 of the detector 24. And the two-photon excitation fluorescence having a wavelength which overlaps that of the coherent Stokes Raman scattering light, and the coherent anti-Stokes Raman scattering light are received together by the detection means 8' via the distributed element 27, the distributed projection lens 28, and the shading component 29.

The light received by the detection means 8' is converted photo-electrically, and then it is sent to the lock-in detector 53. The signal sent to the lock-in detector 53 is separated to a signal having AC component modulated and a signal having DC component which has not been modulated, and then, they are detected. Thereby, the modulated coherent anti-Stokes Raman scattering light and the two-photon excitation fluorescence to which has not been modulated in the wavelength zone overlapping with that of the coherent anti-Stokes Raman scattering light, are separated respectively, and then they are extracted and detected.

Thus, according to the microscope of the seventh embodiment, the observation techniques by the second harmonic wave, the two-photon excitation fluorescence, and the coherent Raman scattering light can be used in parallel. However, in a microscope observation, there is a case that all the observation techniques mentioned above may not be needed according to the area of interest of the observation object. Irradiation of the laser light by the laser pulse irradiation means may give damage to the specimen. Furthermore, it also becomes a cause of fading of fluorescence. Therefore, it is desired that irradiation by the laser pulse irradiation means is small as much as possible responding to an observation technique.

However, according to the microscope of the sixth embodiment, irradiation of the laser light can be suppressed to necessary minimum responding to the observation technique according to the area of interest of the observation object since it is constituted so as to enable to select the laser light required for observation by arranging the laser combiner 61 and the controller 62.

Switching of the laser light according to the observation technique, is carried out by switching of combinations of the laser pulse irradiation means 1', 2' and 65 for the laser pulse to be irradiated, via the controller 62 by driving the acoustic optical elements 63, 64, and 66. Each of observation techniques in the microscope of the sixth embodiment, and the combinations of the laser pulse generating means and the detection means to be selected corresponding to observation techniques is shown in Table 1. In Table 1, CARS denotes the coherent anti-Stokes Raman scattering light observation, 2-P denotes the two-photon excitation fluorescence observation, SHG denotes the second harmonic wave observation, and 1-P denotes the single photon excitation fluorescence observation.

TABLE 1

| Observation technique | Pump light | Stokes light | Single photon excitation light | Detection means |
|---|---|---|---|---|
| CARS | ON | ON | OFF | Detection means 8' |
| 2-P | OFF | ON | OFF | Detection means 9''' |
|  |  |  |  | Detection means 8' |
| SHG | OFF | ON | OFF | Detection means 7''' |
| 1-P | OFF | OFF | ON | Detection means 9''' |
|  |  |  |  | Detection means 8' |

As shown in Table 1, if only the second pulsed laser (the Stokes light) generating means 2' is turned ON, even if the first pulsed laser (the pump light) generating means 1' is turned to OFF, the forward two-photon excitation fluorescence can be detected by the detection means 9''', the vertically illuminated two-photon excitation fluorescence can be detected by the detection means 8', and the forward second harmonic can be detected by the detection means 7''', respectively. When either the pump light or the Stokes light is set to OFF, the lock-in detector 53 also becomes to OFF, and the two-photon excitation fluorescence having a wavelength zone in which the coherent anti-Stokes Raman scattering light and a wavelength do not overlap, or the single photon excitation fluorescence can be detected by the detection means 8' as shown the Table 1.

Thus, according to the microscope of the sixth embodiment, responding to the area of interest of observation object, observation techniques can be switched with necessary minimum amount of the laser irradiation light.

According to the microscope of the sixth embodiment, the laser combiner 61 and the controller 62 are used for the microscope of the constitution in which the CARS light can be detected. But, they can be used for the microscope having a constitution by which the CSRS light can be detected as shown in the embodiments 1 or 2.

Seventh Embodiment

Figure 15:
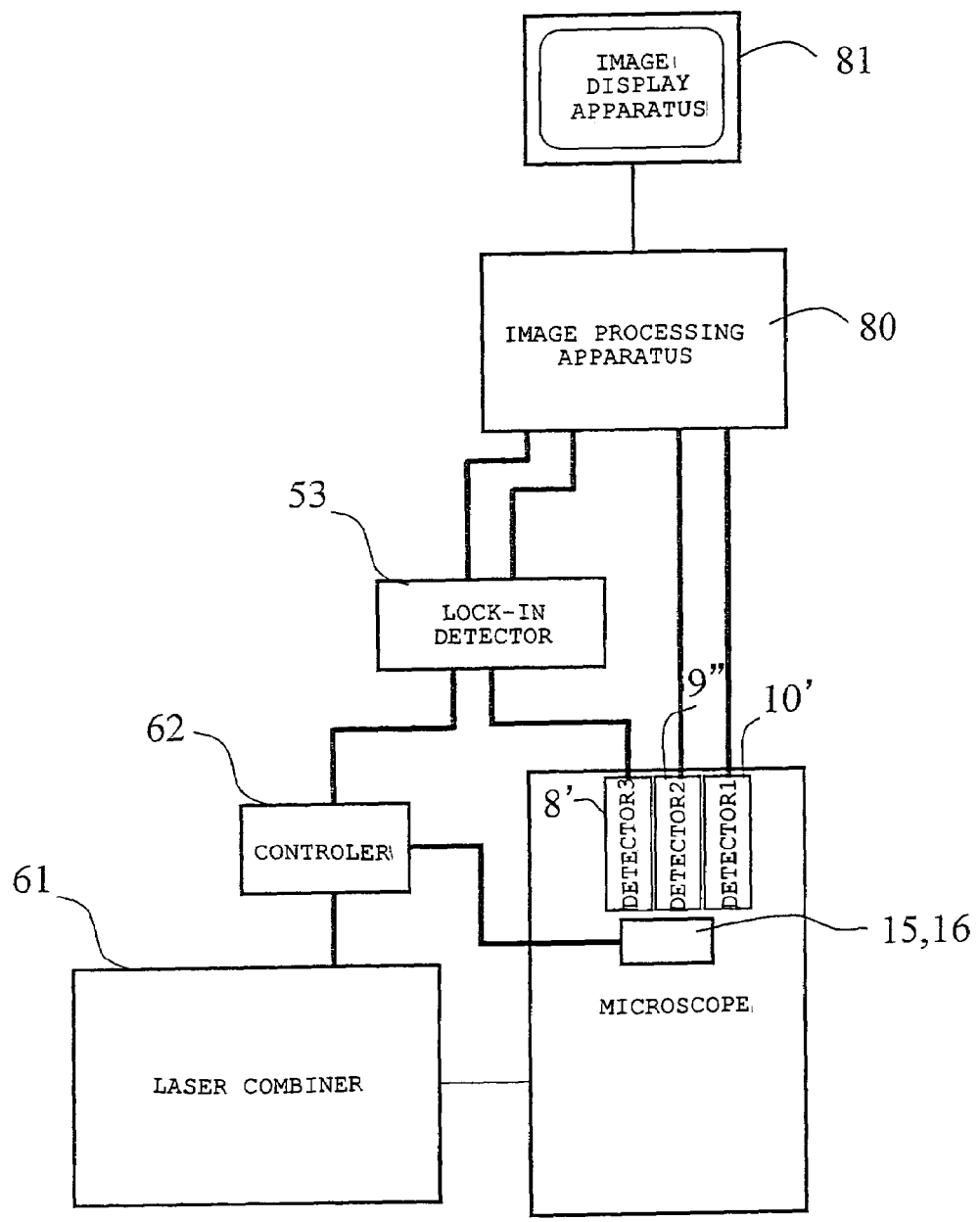
FIG. 15 is a diagram showing an optical composition of the microscope system of the seventh embodiment according to the present invention.
Figure 16A:
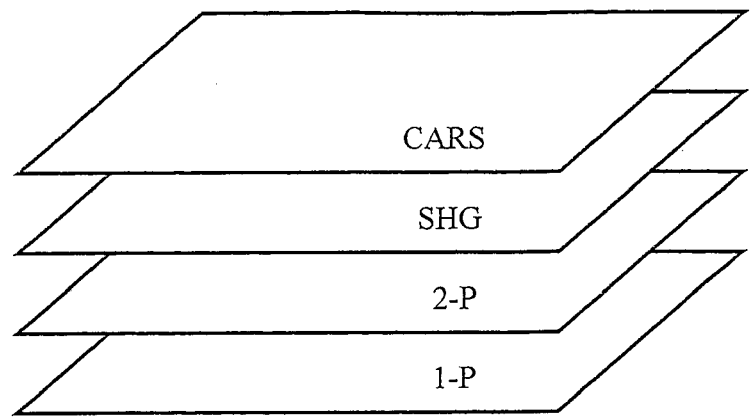
FIG. 16A is an explanatory diagram showing an example, wherein with respect to a display form of an image displayed by each of observation light in the image display apparatus according to the microscope of the seventh embodiment, the image by each of the observation technique is displayed on a full screen by switching.
Figure 16B:
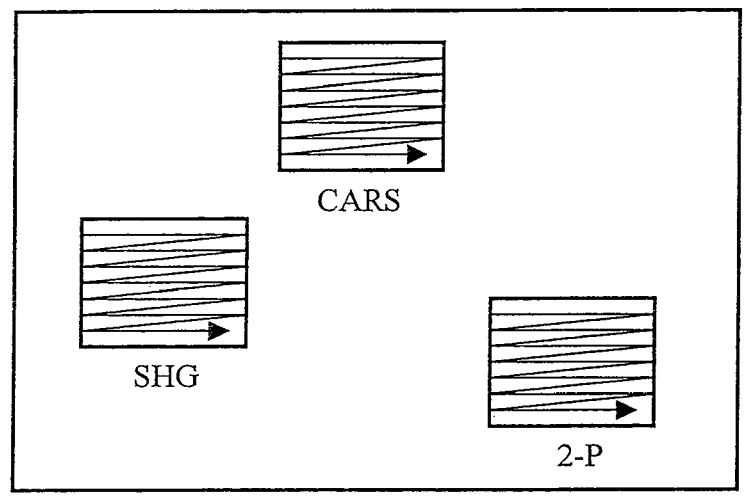
FIG. 16B is an explanatory diagram showing an example, wherein with respect to a display form of an image displayed by each of observation light in the image display apparatus according to the microscope of the seventh embodiment, when each of images of the coherent Raman scattering light, the second harmonic wave, and the two-photon excitation fluorescence is scanned for every area of interest of the object of observation in a display screen.
Figure 16C:
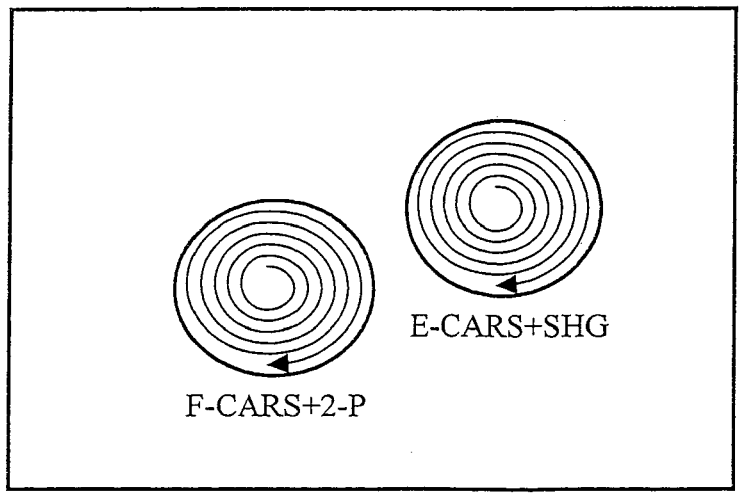
FIG. 16C is an explanatory diagram showing an example, wherein with respect to a display form of an image displayed by each of observation light in the image display apparatus according to the microscope of the seventh embodiment, different observation techniques in the same area of interest of the object of observation within a display surface are combined and scanned.

FIG. 15 is a diagram showing an optical composition of the microscope system of the seventh embodiment according to the present invention. FIG. 16 is a diagram showing an example of a display form of each observation light in a picture displayed by the image display apparatus of the microscope of the seventh embodiment. FIG. 16A is a diagram showing an example when the image by each observation technique is switched to display on the full screen. FIG. 16B is a diagram showing an example when in every area of interest of observation object in the display screen, the coherent Raman scattering light, the second harmonic wave, and the image of two-photon excitation fluorescence are scanned. FIG. 16C, is a diagram showing an example when in the same area of interest of observation object in the display screen, scanning is carried out by combining different observation techniques.

A microscope of the seventh embodiment, comprises, in addition to the constitution of the microscope of the sixth embodiment, the coherent anti-Stokes Raman scattering photon detection means, the two-photon excitation fluorescence detection means, an image processing apparatus 80 which processes the signal detected by the second harmonic wave detection means, an image display apparatus 81 which displays the picture processed by the image processing apparatus 80.

The controller 62 is connected to the galvanometer mirrors 15 and 16 which are equipped on the main body of the microscope. And the controller 62 has a function which controls the laser combiner 61 and the galvanometer mirrors 15 and 16, so that via the image processing apparatus 80 and the image display apparatus 81, at a desired part in a screen, an observation image by the coherent anti-Stokes Raman scattering light, an observation image by the two-photon excitation fluorescence, and an observation image by the second harmonic wave are displayed, According to the microscope of the seventh embodiment constituted in this way, responding to an area of interest of observation object, an observation using various observation techniques can be carried out by single display screen. For example, in each of observation techniques, via the galvanometer mirrors 15 and 16, sequential scanning of the whole area of observation object can be carried out. By this way, as shown in FIG. 16A, in each of display screens of the image display apparatus 81, each of images of the two-photon excitation fluorescence, the second harmonic wave, the CARS light or the CSRS light, and the single photon excitation fluorescence can be switched and displayed, respectively.

For example, in each of the areas of interest of observation object observation techniques can be switched, and vector scanning can be carried out via the galvanometer mirrors 15 and 16. By this way, as shown in FIG. 16B, in the display screen of the image display apparatus 81, in each of areas of interest of observation object, an image of the two-photon excitation fluorescence, the second harmonic wave, the CARS light or the CSRS light, and the single photon excitation fluorescence can be displayed.

Further, for example, in each of the areas of interest of observation object, two or more observation techniques can be combined by switching, and vector scanning can be carried out via the galvanometer mirrors 15 and 16. By this way, as shown in FIG. 16C, in each of the areas of interest of observation object, on the display screen of the image display apparatus 81, in each of the areas of interest of observation object, a combination of the image of a desired observation light among the two-photon excitation fluorescence, the second harmonic wave, the CARS light or the CSRS light, and the single photon excitation fluorescence, for example, combination of the F-CARS light and the second harmonic wave, or combination of the E-CARS light and the two-photon excitation fluorescence can be displayed.

Therefore, according to the microscope of the seventh embodiment, for example, with respect to single organism specimen, observations on the same screen can be carried out of a surface layer by using the single photon excitation fluorescence, a depth layer by using the two-photon excitation fluorescence, a collagen and a fiber film by using the second harmonic wave, and protein and a molecule by using the CARS and the CSRS, or observations can be carried out with respect of each of the images by switching each screen.

As for the scanning method of the illuminating radiation for obtaining the image of each observation light by the galvanometer mirrors 15 and 16, any of the sequential scanning of the whole area of observation object mentioned above and the vector scanning for every area of interest of observation object may be used.

When the sequential scanning of the whole area of observation object is carried out, cross talk of observation pictures can be reduced.

When the vector scanning is carried out for every area of interest of observation object, processing speed becomes high.

As the vector scanning, any of point scan, free line scan, tornado scan, etc. can be used.

Furthermore, responding to observation techniques, it is good to control to enable to change the scanning rate of the galvanometer mirrors 15 and 16 by the controller 62, for example, in each of screens of the sequential scanning, or in each of ROI of the vector scanning.

An amount of the light detected by an observation technique differs. Therefore, when a scanning rate is made the same regardless of an observation technique, there is a case that an amount of the light detected by the observation technique becomes short, or a case that it may become excessive. If a scanning rate ca be changed, the amount of the light detected is adjusted accordingly, it becomes easy to observe the detection light image by each observation technique.

For the same purpose, responding to observation techniques, it is constituted such that the number of times of scanning by the galvanometer mirrors 15 and 16 can be changed, or irradiation output of the laser light according to an observation technique can be changed. It is desired that the output of the laser can be adjusted by the pulsed laser generating means itself, or can be adjusted by using a acoustic optical element, etc.

Furthermore, responding to observation techniques, it can be constituted such that a part of pulses of the laser light is removed using a pulse picker etc.

The microscope of the seventh embodiment is constituted by adding the image processing apparatus 80 and the image display apparatus 81 and the like, on the basis of the microscope of the sixth embodiment. However, the microscope of the present invention is not limited to such constitution, and may be constituted based on the microscope of any embodiments mentioned above.

As it has been clear by explanations mentioned above, according to the present invention, to observe to single specimen, responding to the purpose, it is possible to obtain the microscope by which any of the multi-photon excitation fluorescence observation, the second harmonic wave observation, and the coherent Raman scattering light observations can be carried out in parallel, or selectively.

The invention claimed is:

1. A microscope comprising:
a first pulsed laser generating means that generates first pulse light having a first wavelength,
a second pulsed laser generating means that generates second pulse light having a second wavelength,
an irradiation means constructed and arranged to synthesize the first pulse light and the second pulse light for irradiating a specimen with synthesized light,
a coherent Raman scattering light extraction means for extracting coherent Raman scattering light from light emanating from the specimen irradiated with light via the irradiation means,
a multiphoton excitation fluorescence extraction means for extracting multiphoton excitation fluorescence generated by irradiation of the specimen with the second pulse light, from the light emanating from the specimen irradiated with light via the irradiation means,
a second-harmonic wave extraction means for extracting second-harmonic wave generated by irradiation of the specimen with the second pulse light, from the light emanating from the specimen irradiated with light via the irradiation means,
a coherent Raman scattering photon detection means for detecting the coherent Raman scattering light extracted via the coherent Raman scattering light extraction means,
a multiphoton excitation fluorescence detection means for detecting the multiphoton excitation fluorescence extracted via the multiphoton excitation fluorescence extraction means, and
a second-harmonic wave detection means for detecting the second-harmonic wave extracted via the second-harmonic wave extraction means.

2. A microscope comprising:
a first pulsed laser generating means that generates first pulse light having a first wavelength,
a second pulsed laser generating means that generates second pulse light having a second wavelength,
an irradiation means constructed and arranged to synthesize the first pulse light and the second pulse light for irradiating a specimen with synthesized light,
a coherent Raman scattering light extraction means for extracting coherent Raman scattering light, from light emanating from the specimen irradiated with light via the irradiation means,
an epi-illuminated multiphoton excitation fluorescence extraction means for extracting multiphoton excitation fluorescence generated by irradiation of the specimen with the second pulse light, from light emanating from the specimen in a reflecting direction, which is defined as a direction in which light for irradiation incident on the specimen via the irradiation means is reflected,
a forward second-harmonic wave extraction means for extracting second-harmonic wave generated by irradiation of the specimen with the second pulse light, from light emanating from the specimen in a transmitting direction, which is defined as a direction in which light for irradiation incident on the specimen via the irradiation means is transmitted,
a coherent Raman scattering photon detection means for detecting the coherent Raman scattering light extracted via the coherent Raman scattering light extraction means,
an epi-illuminated multiphoton excitation fluorescence detection means for detecting the multiphoton excitation fluorescence extracted via the epi-illuminated multiphoton excitation fluorescence extraction means, and
a forward second-harmonic wave detection means for detecting the second-harmonic wave extracted via the forward second-harmonic wave extraction means.

3. A microscope comprising,
a first pulsed laser generating means that generates first pulse light having a first wavelength,
a second pulsed laser generating means that generates second pulse light having a second wavelength,
an irradiation means constructed and arranged to synthesize the first pulse light and the second pulse light for irradiating a specimen with synthesized light,
a coherent Raman scattering light extraction means for extracting coherent Raman scattering light, from light emanating from the specimen irradiated with light via the irradiation means,
an epi-illuminated second-harmonic wave extraction means for extracting second-harmonic wave generated by irradiation of the specimen with the second pulse light, from light emanating from the specimen in a reflecting direction, which is defined as a direction in which light for irradiation incident on the specimen via the irradiation means is reflected, a forward multiphoton excitation fluorescence extraction means for extracting multiphoton excitation fluorescence generated by irradiation of the specimen with the second pulse light, from light emanating from the specimen in a transmitting direction, which is defined as a direction in which light for irradiation incident on the specimen via the irradiation means is transmitted, a coherent Raman scattering photon detection means for detecting the coherent Raman scattering light extracted via the coherent Raman scattering light extraction means, a forward multiphoton excitation fluorescence detection means for detecting the multiphoton excitation fluorescence extracted via the forward multiphoton excitation fluorescence extraction means, and an epi-illuminated second-harmonic wave detection means for detecting the second-harmonic wave extracted via the epi-illuminated second-harmonic wave extraction means.

4. A microscope comprising:

a first pulsed laser generating means that generates first pulse light having a first wavelength, a second pulsed laser generating means that generates second pulse light having a second wavelength, an irradiation means constructed and arranged to synthesize the first pulse light and the second pulse light for irradiating a specimen with synthesized light, a coherent Raman scattering light extraction means for extracting coherent Raman scattering light, from light emanating from the specimen irradiated with light via the irradiation means, an epi-illuminated, second-harmonic wave/multiphoton excitation fluorescence switching/extraction means for extracting, upon switching, second-harmonic wave generated by irradiation of the specimen with the second pulse light or multiphoton excitation fluorescence generated by irradiation of the specimen with the second pulse light, from light emanating from the specimen in a reflecting direction, which is defined as a direction in which light for irradiation incident on the specimen via the irradiation means is reflected, a forward, second-harmonic wave/multiphoton excitation fluorescence switching/extraction means for extracting, upon switching, second-harmonic wave generated by irradiation of the specimen with the second pulse light or multiphoton excitation fluorescence generated by irradiation of the specimen with the second pulse light, from light emanating from the specimen in a transmitting direction, which is defined as a direction in which light for irradiation incident on the specimen via the irradiation means is transmitted, a coherent Raman scattering photon detection means for detecting the coherent Raman scattering light extracted via the coherent Raman scattering light extraction means, an epi-illuminated switched and extracted light detection means for detecting light extracted via the epi-illuminated, second-harmonic wave/multiphoton excitation fluorescence switching/extraction means, and a forward switched and extracted light detection means for detecting light extracted via the forward second-harmonic wave/multiphoton excitation fluorescence switching/extraction means.

5. A microscope comprising:

a first pulsed laser generating means that generates first pulse light having a first wavelength, a second pulsed laser generating means that generates second pulse light having a second wavelength, an irradiation means constructed and arranged to synthesize the first pulse light and the second pulse light for irradiating a specimen with synthesized light, a coherent Raman scattering light extraction means for extracting coherent Raman scattering light, from light emanating from the specimen irradiated with light via the irradiation means, an epi-illuminated multiphoton excitation fluorescence extraction means for extracting multiphoton excitation fluorescence generated by irradiation of the specimen with the second pulse light, from light emanating from the specimen in a reflecting direction, which is defined as a direction in which light for irradiation incident on the specimen via the irradiation means is reflected, an epi-illuminated second-harmonic wave extraction means for extracting second-harmonic wave generated by irradiation of the specimen with the second pulse light, from the light emanating from the specimen in the reflecting direction, a coherent Raman scattering photon detection means for detecting the coherent Raman scattering light extracted via the coherent Raman scattering light extraction means, an epi-illuminated multiphoton excitation fluorescence detection means for detecting the multiphoton excitation fluorescence extracted via the epi-illuminated multiphoton excitation fluorescence extraction means, an epi-illuminated second-harmonic wave detection means for detecting the second-harmonic wave extracted via the epi-illuminated second-harmonic wave extraction means, a forward multiphoton excitation fluorescence extraction means for extracting multiphoton excitation fluorescence generated by irradiation of the specimen with the second pulse light, from light emanating from the specimen in a transmitting direction, which is defined as a direction in which light for irradiation incident on the specimen via the irradiation means is transmitted, a forward second-harmonic wave extraction means for extracting second-harmonic wave generated by irradiation of the specimen with the second pulse light, from light emanating from the specimen in the transmitting direction, a forward multiphoton excitation fluorescence detection means for detecting the multiphoton excitation fluorescence extracted via the forward multiphoton excitation fluorescence extraction means, and a forward second-harmonic wave detection means for detecting the second-harmonic wave extracted via the forward second-harmonic wave extraction means.

6. The microscope according to claim 1, wherein:

a predetermined wavelength band having wavelengths close to and shorter than the first wavelength of the first pulse light is scanned by the second pulse light, and the coherent Raman scattering light is coherent Stokes Raman scattering light.

7. The microscope according to claim 1, wherein:

a predetermined wavelength band having wavelengths close to and longer than the first wavelength of the first pulse light is scanned by the second pulse light, the coherent Raman scattering light is coherent anti-Stokes Raman scattering light with the coherent Raman scattering light extraction means being configured as a coherent anti-Stokes Raman scattering light extraction means, and a multiphoton excitation fluorescence/CARS light separation means is provided for separating the multiphoton excitation fluorescence from the coherent anti-Stokes Raman scattering light in a situation where a wavelength band of the multiphoton excitation fluorescence and a wavelength band of the coherent anti-Stokes Raman scattering light may overlap at least partially.

8. The microscope according to claim 7, wherein the multiphoton excitation fluorescence/CARS light separation means comprises the coherent anti-Stokes Raman scattering light extraction means that has a time decomposition separation means for separating the multiphoton excitation fluorescence and the coherent anti-Stokes Raman scattering light by time decomposition.

9. The microscope according to claim 8, wherein the time decomposition separation means comprises:
a Kerr gate which changes a polarization direction of linear polarized light transmitted therethrough when gate light is incident thereon obliquely,
a gate light incidence means which introduces the second pulse light, as the gate light, to be incident on the Kerr gate obliquely, at a same timing as a timing of the coherent anti-Stokes Raman scattering light entering the Kerr gate,
a first polarization component that changes the multiphoton excitation fluorescence into linear polarized light, and
a second polarization component constructed and arranged to transmit linear polarized light, that has been changed in polarization direction by being transmitted through the Kerr gate and to intercept linear polarized light that remains unchanged in polarization direction while being transmitted through the Kerr gate.

10. The microscope according to claim 7, wherein the multiphoton excitation fluorescence/CARS light separation means comprises:
a modulation means which generates modulated coherent anti-Stokes Raman scattering light, and
a detection device, which serves as both of the coherent anti-Stokes Raman scattering photon detection means and the multiphoton excitation fluorescence detection means, constructed and arranged to receive both the modulated coherent anti-Stokes Raman scattering light and the multiphoton excitation fluorescence and to detect a modulated component and a non-modulated component separately from the received light.

11. The microscope according to claim 10, wherein:
the modulation means comprises a modulator for modulating the first pulse light, and the detection device comprises a lock-in detector.

12. The microscope according to claim 1, wherein:
a predetermined wavelength band is scanned by the first pulse light, and
the second pulse light is fixed to an optimal wavelength for multiphoton excitation.

13. The microscope according to claim 1, further comprising:
a laser light selection means for switching ON/OFF the first pulsed laser generating means; and the second pulsed laser generating means, and
a control means for controlling the laser light selection means.

14. The microscope according to claim 13, further comprising:
an image processing apparatus for processing signals detected via the coherent Raman scattering photon detection means, the multiphoton excitation fluorescence detection means, and the second-harmonic wave detection means,
an image display apparatus which displays a picture processed by the image processing apparatus, and
a scanning means for causing light for irradiation to scan the specimen two-dimensionally,
wherein the control means controls the laser light selection means and the scanning means so that an observation image by the coherent anti-Stokes Raman scattering light, an observation image by the multiphoton excitation fluorescence, and an observation image by the second-harmonic wave can be displayed in parallel or selectively at a position on a display screen of the image display apparatus corresponding to an area of interest of the specimen.

15. The microscope according to claim 1, wherein:
the first pulsed laser generating means is a pulsed laser light source that oscillates a pulsed laser beam having a pulse width of picosecond, and
the second pulse laser generating means is a pulsed laser light source that oscillates a pulsed laser beam having a pulse width of femtosecond.

16. The microscope according to claim 1, wherein the coherent Raman scattering light extraction means is constructed and arranged so that
a mode for performing extraction of coherent Raman scattering light from light emanating from the specimen in a reflecting direction, which is defined as a direction in which light for irradiation incident on the specimen via the irradiation means is reflected,
a mode for performing extraction of coherent Raman scattering light from light emanating from the specimen in a transmitting direction, which is defined as a direction in which light for irradiation incident on the specimen via the irradiation means is transmitted, and a mode for performing both of the extraction of the coherent Raman scattering light from light emanating from the specimen in the reflecting direction and the extraction of the coherent Raman scattering light from light emanating from the specimen in the transmitting direction are switchable.

17. The microscope according to claim 2, wherein:
a predetermined wavelength band having wavelengths close to and shorter than the first wavelength of the first pulse light is scanned by the second pulse light, and
the coherent Raman scattering light is coherent Stokes Raman scattering light.

18. The microscope according to claim 3, wherein:
a predetermined wavelength band having wavelengths close to and shorter than the first wavelength of the first pulse light is scanned by the second pulse light, and
the coherent Raman scattering light is coherent Stokes Raman scattering light.

19. The microscope according to claim 4, wherein:
a predetermined wavelength band having wavelengths close to and shorter than the first wavelength of the first pulse light is scanned by the second pulse light, and
the coherent Raman scattering light is coherent Stokes Raman scattering light.

20. The microscope according to claim 5, wherein:
a predetermined wavelength band having wavelengths close to and shorter than the first wavelength of the first pulse light is scanned by the second pulse light, and
the coherent Raman scattering light is coherent Stokes Raman scattering light.

21. The microscope according to claim 1, wherein:
by simultaneously absorbing a plurality (number n) of photons in the second pulsed light having the second wavelength λ, fluorescence substance contained in the specimen is excited by a wavelength λ/n, to generate the multiphoton excitation fluorescence, which has a wavelength a little longer than the wavelength λ/n, and
a wavelength of the second-harmonic wave is half the second wavelength λ of the second pulse light.

22. The microscope according to claim 2, wherein:
by simultaneously absorbing a plurality (number n) of photons in the second pulsed light having the second wavelength λ, fluorescence substance contained in the specimen is excited by a wavelength λ/n, to generate the multiphoton excitation fluorescence, which has a wavelength a little longer than the wavelength λ/n, and
a wavelength of the second-harmonic wave is half the second wavelength λ of the second pulse light.

23. The microscope according to claim 3, wherein:
by simultaneously absorbing a plurality (number n) of photons in the second pulsed light having the second wavelength λ, fluorescence substance contained in the specimen is excited by a wavelength λ/n, to generate the multiphoton excitation fluorescence, which has a wavelength a little longer than the wavelength λ/n, and
a wavelength of the second-harmonic wave is half the second wavelength λ of the second pulse light.

24. The microscope according to claim 4, wherein:
by simultaneously absorbing a plurality (number n) of photons in the second pulsed light having the second wavelength λ, fluorescence substance contained in the specimen is excited by a wavelength λ/n, to generate the multiphoton excitation fluorescence, which has a wavelength a little longer than the wavelength λ/n, and
a wavelength of the second-harmonic wave is half the second wavelength λ of the second pulse light.

25. The microscope according to claim 5, wherein:
by simultaneously absorbing a plurality (number n) of photons in the second pulsed light having the second wavelength λ, fluorescence substance contained in the specimen is excited by a wavelength λ/n, to generate the multiphoton excitation fluorescence, which has a wavelength a little longer than the wavelength λ/n, and
a wavelength of the second-harmonic wave is half the second wavelength λ of the second pulse light.

26. A microscope, comprising:
first pulse light having a first wavelength and second pulse light having a second wavelength generated by a pulsed laser generating means,
an irradiation means constructed and arranged to synthesize the first pulse light and the second pulse light for irradiating a specimen with synthesized light,
a coherent Raman scattering light extraction means for extracting coherent Raman scattering light, from light emanating from the specimen irradiated with light via the irradiation means,
a multiphoton excitation fluorescence extraction means for extracting multiphoton excitation fluorescence generated by irradiation of the specimen with the second pulse light, from the light emanating from the specimen irradiated with light via the irradiation means,
a second-harmonic wave extraction means for extracting second-harmonic wave generated by irradiation of the specimen with the second pulse light, from the light emanating from the specimen irradiated with light via the irradiation means,
a coherent Raman scattering photon detection means for detecting the coherent Raman scattering light extracted via the coherent Raman scattering light extraction means,
a multiphoton excitation fluorescence detection means for detecting the multiphoton excitation fluorescence extracted via the multiphoton excitation fluorescence extraction means, and
a second-harmonic wave detection means for detecting the second-harmonic wave extracted via the second-harmonic wave extraction means.

27. A microscope, comprising:
first pulse light having a first wavelength and second pulse light having a second wavelength generated by a pulsed laser generating means,
an irradiation means constructed and arranged to synthesize the first pulse light and the second pulse light for irradiating a specimen with synthesized light,
coherent Raman scattering light extraction means for extracting coherent Raman scattering light, from light emanating from the specimen irradiated with light via the irradiation means,
an epi-illuminated multiphoton excitation fluorescence extraction means for extracting multiphoton excitation fluorescence generated by irradiation of the specimen with the second pulse light, from light emanating from the specimen in a reflecting direction, which is defined as a direction in which light for irradiation incident on the specimen via the irradiation means is reflected,
a forward second-harmonic wave extraction means for extracting second-harmonic wave generated by irradiation of the specimen with the second pulse light, from light emanating from the specimen in a transmitting direction, which is defined as a direction in which light for irradiation incident on the specimen via the irradiation means is transmitted,
a coherent Raman scattering photon detection means for detecting the coherent Raman scattering light extracted via the coherent Raman scattering light extraction means,
an epi-illuminated multiphoton excitation fluorescence detection means for detecting the multiphoton excitation fluorescence extracted via the epi-illuminated multiphoton excitation fluorescence extraction means, and
a forward second-harmonic wave detection means for detecting the second-harmonic wave extracted via the forward second-harmonic wave extraction means.

28. A microscope, comprising:
first pulse light having a first wavelength and second pulse light having a second wavelength generated by a pulsed laser generating means,
an irradiation means constructed and arranged to synthesize the first pulse light and the second pulse light for irradiating a specimen with synthesized light,
a coherent Raman scattering light extraction means for extracting coherent Raman scattering light, from light emanating from the specimen irradiated with light via the irradiation means,
an epi-illuminated second-harmonic wave extraction means for extracting second-harmonic wave generated by irradiation of the specimen with the second pulse light, from light emanating from the specimen in a reflecting direction, which is defined as a direction in which light for irradiation incident on the specimen via the irradiation means is reflected,
a forward multiphoton excitation fluorescence extraction means for extracting multiphoton excitation fluorescence generated by irradiation of the specimen with the second pulse light, from light emanating from the specimen in a transmitting direction, which is defined as a direction in which light for irradiation incident on the specimen via the irradiation means is transmitted, a coherent Raman scattering photon detection means for detecting the coherent Raman scattering light extracted via the coherent Raman scattering light extraction means, a forward multiphoton excitation fluorescence detection means for detecting the multiphoton excitation fluorescence extracted via the forward multiphoton excitation fluorescence extraction means, and an epi-illuminated second-harmonic wave detection means for detecting the second-harmonic wave extracted via the epi-illuminated second-harmonic wave extraction means.

29. A microscope, comprising:

first pulse light having a first wavelength and second pulse light having a second wavelength generated by a pulsed laser generating means, an irradiation means constructed and arranged to synthesize the first pulse light and the second pulse light for irradiating a specimen with synthesized light, a coherent Raman scattering light extraction means for extracting coherent Raman scattering light, from light emanating from the specimen irradiated with light via the irradiation means, an epi-illuminated, second-harmonic wave/multiphoton excitation fluorescence switching/extraction means for extracting, upon switching, second-harmonic wave generated by irradiation of the specimen with the second pulse light or multiphoton excitation fluorescence generated by irradiation of the specimen with the second pulse light, from light emanating from the specimen in a reflecting direction, which is defined as a direction in which light for irradiation incident on the specimen via the irradiation means is reflected, a forward, second-harmonic wave/multiphoton excitation fluorescence switching/extraction means for extracting, upon switching, second-harmonic wave generated by irradiation of the specimen with the second pulse light or multiphoton excitation fluorescence generated by irradiation of the specimen with the second pulse light, from light emanating from the specimen in a transmitting direction, which is defined as a direction in which light for irradiation incident on the specimen via the irradiation means is transmitted, a coherent Raman scattering photon detection means for detecting the coherent Raman scattering light extracted via the coherent Raman scattering light extraction means, an epi-illuminated switched and extracted light detection means for detecting light extracted via the epi-illuminated, second-harmonic wave/multiphoton excitation fluorescence switching/extraction means, and a forward switched and extracted light detection means for detecting light extracted via the forward second-harmonic wave/multiphoton excitation fluorescence switching/extraction means.

30. A microscope, comprising:

first pulse light having a first wavelength and second pulse light having a second wavelength generated by a pulsed laser generating means, an irradiation means constructed and arranged to synthesize the first pulse light and the second pulse light for irradiating a specimen with synthesized light, a coherent Raman scattering light extraction means for extracting coherent Raman scattering light, from light emanating from the specimen irradiated with light via the irradiation means, an epi-illuminated multiphoton excitation fluorescence extraction means for extracting multiphoton excitation fluorescence generated by irradiation of the specimen with the second pulse light, from light emanating from the specimen in a reflecting direction, which is defined as a direction in which light for irradiation incident on the specimen via the irradiation means is reflected, an epi-illuminated second-harmonic wave extraction means for extracting second-harmonic wave generated by irradiation of the specimen with the second pulse light, from the light emanating from the specimen in the reflecting direction, a coherent Raman scattering photon detection means for detecting the coherent Raman scattering light extracted via the coherent Raman scattering light extraction means, an epi-illuminated multiphoton excitation fluorescence detection means for detecting the multiphoton excitation fluorescence extracted via the epi-illuminated multiphoton excitation fluorescence extraction means, an epi-illuminated second-harmonic wave detection means for detecting the second-harmonic wave extracted via the epi-illuminated second-harmonic wave extraction means, a forward multiphoton excitation fluorescence extraction means for extracting multiphoton excitation fluorescence generated by irradiation of the specimen with the second pulse light, from light emanating from the specimen in a transmitting direction, which is defined as a direction in which light for irradiation incident on the specimen via the irradiation means is transmitted, a forward second-harmonic wave extraction means for extracting second-harmonic wave generated by irradiation of the specimen with the second pulse light, from light emanating from the specimen in the transmitting direction, a forward multiphoton excitation fluorescence detection means for detecting the multiphoton excitation fluorescence extracted via the forward multiphoton excitation fluorescence extraction means, and a forward second-harmonic wave detection means for detecting the second-harmonic wave extracted via the forward second-harmonic wave extraction means.

* * * * *